United States Patent
Greenfield

(10) Patent No.: US 9,892,237 B2
(45) Date of Patent: Feb. 13, 2018

(54) SYSTEM AND METHOD FOR CHARACTERIZING BIOLOGICAL SEQUENCE DATA THROUGH A PROBABILISTIC DATA STRUCTURE

(71) Applicant: Reference Genomics, Inc., San Francisco, CA (US)

(72) Inventor: Nicholas Boyd Greenfield, San Francisco, CA (US)

(73) Assignee: Reference Genomics, Inc., San Francisco, CA (US)

( * ) Notice: Subject to any disclaimer, the term of this patent is extended or adjusted under 35 U.S.C. 154(b) by 0 days.

(21) Appl. No.: 14/615,672

(22) Filed: Feb. 6, 2015

(65) Prior Publication Data
US 2015/0220684 A1      Aug. 6, 2015

Related U.S. Application Data

(60) Provisional application No. 61/936,521, filed on Feb. 6, 2014.

(51) Int. Cl.
*G06F 19/00* (2011.01)

(52) U.S. Cl.
CPC .................................. *G06F 19/70* (2013.01)

(58) Field of Classification Search
CPC ....... H04L 67/10; H04L 9/14; G06F 21/6218; G06F 17/30; G06F 17/3012; G06F 17/30424; G06F 17/30289; G06F 17/3033; G06F 17/30345; G06F 17/30483; G06F 17/30554; G06F 17/30563; G06F 17/30584
See application file for complete search history.

(56) References Cited

PUBLICATIONS

Abadi et al. The VLDB Journal—The International Journal on Very Large Data Bases vol. 18 Issue 2 Apr. 2009.*
Pieterse, "Performance of C++ Bit-vector Implementations," In Proceedings of the 2010 Annual Research Conference of the South African Institute of Computer Scientists and Information Technologists, p. 242-250, 2010.*
Brudno, "Fast and sensitive multiple alignment of large genomic sequences," BMC bioinformatics, vol. 4(1), p. 66, 2003.*
Lin, "Coordinating computation and i/o in massively parallel sequence search," IEEE Transactions on Parallel and Distributed Systems, vol. 22(4), p. 529-543, 2011.*
Stranneheim, "Classification of DNA sequences using Bloom filters," BioInformatics, vol. 26(13), p. 1595-1600, 2010.*
Stranneheim, Henrik et al., "Classification of DNA sequences using Bloom filters", Bioinformatics, Jul. 1, 2010, vol. 26, Issue 13, p. 1595-1600.

* cited by examiner

*Primary Examiner* — G. Steven Vanni
(74) *Attorney, Agent, or Firm* — Alpine Patents LLC; Brian Van Osdol

(57) ABSTRACT

A system and method for resolving data through a probabilistic data structure can include initializing a B-field data structure, inserting a key-value element into the B-field data structure, selecting at least one key query, and looking up the value of a key lookup request through the B-field data structure.

25 Claims, 21 Drawing Sheets

Sample bit array with previous inserts:

| 0 | | | | | | | | | | 10 | | | | | | | | | |
|---|---|---|---|---|---|---|---|---|---|---|---|---|---|---|---|---|---|---|---|
| 0 | 0 | 1 | 0 | 0 | 1 | 1 | 1 | 0 | 0 | 0 | 1 | 0 | 0 | 0 | 1 | 0 | 0 | 1 | 0 |

| 20 | | | | | | | | | | 30 | | | | | | | | | |
|---|---|---|---|---|---|---|---|---|---|---|---|---|---|---|---|---|---|---|---|
| 0 | 1 | 0 | 0 | 0 | 1 | 1 | 0 | 1 | 0 | 0 | 0 | 1 | 1 | 0 | 1 | 1 | 0 | 0 | 1 |

| 40 | | | | | | | | | | 50 | | | | | | | | | |
|---|---|---|---|---|---|---|---|---|---|---|---|---|---|---|---|---|---|---|---|
| 1 | 1 | 0 | 0 | 1 | 0 | 1 | 0 | 0 | 0 | 0 | 0 | 1 | 1 | 1 | 1 | 1 | 1 | 1 | 0 |

| 60 | | | | | | | | | | 70 | | | | | | | | | |
|---|---|---|---|---|---|---|---|---|---|---|---|---|---|---|---|---|---|---|---|
| 0 | 0 | 0 | 0 | 1 | 1 | 1 | 1 | 0 | 1 | 0 | 0 | 0 | 0 | 0 | 0 | 1 | 0 | 0 | 1 |

| 80 | | | | | | | | | | 90 | | | | | | | | | |
|---|---|---|---|---|---|---|---|---|---|---|---|---|---|---|---|---|---|---|---|
| 0 | 1 | 0 | 0 | 1 | 1 | 0 | 0 | 0 | 0 | 1 | 0 | 0 | 1 | 1 | 0 | 1 | 0 | 1 | 0 | key123 : 2 h1(key123)= 84    h2(key123)=25
h3(key123)=54    h4(key123)=50       ENCODE(2) = "00101"
h5(key123)=11    h6(key123)=72

Bitwise OR "00101" for each hi((key123) index position:

| 0 | | | | | | | | | | 10 | 11 | | | | | | | | |
|---|---|---|---|---|---|---|---|---|---|---|---|---|---|---|---|---|---|---|---|
| 0 | 0 | 1 | 0 | 0 | 1 | 1 | 1 | 0 | 0 | 0 | 1 | 0 | 1 | 0 | 1 | 0 | 0 | 1 | 0 |

| 20 | | | | | 25 | | | | | 30 | | | | | | | | | |
|---|---|---|---|---|---|---|---|---|---|---|---|---|---|---|---|---|---|---|---|
| 0 | 1 | 0 | 0 | 0 | 1 | 1 | 1 | 1 | 0 | 0 | 0 | 1 | 1 | 0 | 1 | 1 | 0 | 0 | 1 |

| 40 | | | | | | | | | | 50 | | | | 54 | | | | | |
|---|---|---|---|---|---|---|---|---|---|---|---|---|---|---|---|---|---|---|---|
| 1 | 1 | 0 | 0 | 1 | 0 | 1 | 0 | 0 | 0 | 0 | 0 | 1 | 1 | 1 | 1 | 1 | 1 | 1 | 0 |

| 60 | | | | | | | | | | 70 | | 72 | | | | | | | |
|---|---|---|---|---|---|---|---|---|---|---|---|---|---|---|---|---|---|---|---|
| 0 | 0 | 0 | 0 | 1 | 1 | 1 | 1 | 0 | 1 | 0 | 0 | 0 | 0 | 1 | 0 | 1 | 0 | 0 | 1 |

| 80 | | | | 84 | | | | | | 90 | | | | | | | | | |
|---|---|---|---|---|---|---|---|---|---|---|---|---|---|---|---|---|---|---|---|
| 0 | 1 | 0 | 0 | 1 | 1 | 1 | 0 | 1 | 0 | 1 | 0 | 0 | 1 | 1 | 0 | 1 | 0 | 1 | 0 |

This is a mixed/metagenomic sample. 82.34% of 10000 reads were classified using the NCBI RefSeq 65 Complete Genomes database.

Composition overview:

| | |
|---|---|
| High Abundance (0): | *This sample does not contain any dominant species.* |
| Medium Abundance (8): | Vibrio cholerae |
| | Salmonella enterica  (likely subspecies: Salmonella enterica subsp. enterica) |
| | Bacillus cereus  (likely strain: Bacillus cereus ATCC 10987) |
| | Mycobacterium abscessus |
| | Rhodobacter sphaeroides  (likely strain: Rhodobacter sphaeroides 2.4.1) |
| | Staphylococcus aureus  (likely strain: Staphylococcus aureus subsp. aureus HO 5096 0412) |
| | Klebsiella |
| | Enterobacter cloacae  (likely strain: Enterobacter cloacae subsp. cloacae NCTC 9394) |
| Low Abundance (2): | Proteus mirabilis, Citrobacter koseri |

FIGURE 5A

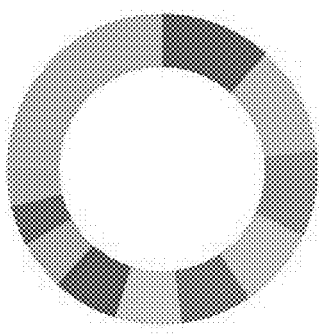

| Readcount | Taxonomic name |
|---|---|
| 28 | Bacteria |
| 10 | Proteobacteria |
| 0 | Alphaproteobacteria |
| 0 | Rhodobacterales |
| 1 | Rhodobacteraceae |
| 0 | Rhodobacter |
| 334 | Rhodobacter sphaeroides |
| 613 | Rhodobacter sphaeroides 2.4.1 |

| Name | Readcount (% of classified reads) |
|---|---|
| Mycobacterium abscessus | 959 (11.65%) |
| Vibrio cholerae | 937 (11.38%) |
| Salmonella enterica subsp. enterica | 738 (8.96%) |
| Enterobacter cloacae subsp. cloacae NCTC 9394 | 704 (8.55%) |
| Rhodobacter sphaeroides 2.4.1 | 613 (7.44%) |
| Staphylococcus aureus | 567 (6.89%) |
| Klebsiella | 563 (6.84%) |
| Bacillus cereus ATCC 10987 | 434 (5.27%) |
| Bacillus cereus | 347 (4.21%) |
| Rhodobacter sphaeroides | 334 (4.06%) |
| (Remaining organisms) | 2038 (24.75%) |

FIGURE 5B

| Organism Name | Rank | Tax ID | % of Classified Reads | % of All Reads | # of Reads | # of Reads (w/ Children) |
|---|---|---|---|---|---|---|
| Mycobacterium abscessus | Species | 36809 | 11.65 | 9.59 | 959 | 959 |
| Vibrio cholerae | Species | 666 | 11.38 | 9.37 | 937 | 988 |
| Salmonella enterica subsp. enterica | Subspecies | 59201 | 8.96 | 7.38 | 738 | 904 |
| Enterobacter cloacae subsp. cloacae NCTC 9394 | Strain | 718254 | 8.55 | 7.04 | 704 | 704 |
| Rhodobacter sphaeroides 2.4.1 | Strain | 272943 | 7.44 | 6.13 | 613 | 613 |
| Staphylococcus aureus | Species | 1280 | 6.89 | 5.67 | 567 | 917 |
| Klebsiella | Genus | 570 | 6.84 | 5.63 | 563 | 923 |
| Bacillus cereus ATCC 10987 | Strain | 222523 | 5.27 | 4.34 | 434 | 434 |
| Bacillus cereus | Species | 1396 | 4.21 | 3.47 | 347 | 782 |
| Rhodobacter sphaeroides | Species | 1063 | 4.06 | 3.34 | 334 | 948 |

FIGURE 5C key query "accggatg"

↓

Hash operator

↓ set of indexes

Lookup operator

&

DECODE([0100...11]) = 347 ⟷ Value-Mapping DB

347:Bacillus cereus
...
434:Bacillus cereus ATCC
...
563:Klebsiella

↓

Bacillus cereus

FIGURE 7B

Biological sequence sample:
accggatggc..................tccgtataat

```
accggatg
 ccggatgg
  cggatggc
   ggatggc.
    gatggc..
     atggc...
      tggc....
       ggc.....
        gc......
         c.......

...

......t
                    ......tc
                    .....tcc
                    ....tccg
                    ...tccgt
                    ..tccgta
                    .tccgtat
                    tccgtata
                     ccgtataa
                      cgtataat
```

Biological sequence k-mers

SEQUENCE LISTING

```
<160> NUMBER OF SEQ ID NOS: 1

<210> SEQ ID NO 1
<211> LENGTH: 10
<212> TYPE: DNA
<213> ORGANISM: Artificial Sequence
<220> FEATURE:
<223> OTHER INFORMATION: For exemplary purposes

<400> SEQUENCE: 1
acgtgcactc                                                          10
```

SYSTEM AND METHOD FOR CHARACTERIZING BIOLOGICAL SEQUENCE DATA THROUGH A PROBABILISTIC DATA STRUCTURE

CROSS-REFERENCE TO RELATED APPLICATIONS

This application claims the benefit of U.S. Provisional Application Ser. No. 61/936,521, filed on 6 Feb. 2014, which is incorporated in its entirety by this reference.

REFERENCE TO AN ELECTRONIC SEQUENCE LISTING

The contents of the electronic sequence listing (1CDX-PatentIn-Sequence-Listing-DOS.txt; Size: 573 bytes; and Date of Creation: 12 Mar. 2015) is herein incorporated by reference in its entirety.

TECHNICAL FIELD

This invention relates generally to the bioinformatics field and more specifically to a new and useful system and method for characterizing biological sequence data through a probabilistic data structure in the bioinformatics field.

BACKGROUND

Scientists and researches have sequenced over one hundred thousand genomes. This has created petabytes of data. Searching such a large database is slow and computationally expensive. Using the common method of Basic Local Alignment Search Tool (or 'BLAST'), searches can take several minutes to hours. Additionally, current search approaches are computationally expensive, requiring large databases and heavy usage of computing resources during searches. In some situations, super computing systems are employed to perform such search processes. The current state of biological sequence search and analysis is slow and expensive. Thus, there is a need in the bioinformatics field to create a new and useful system and method for characterizing biological sequence data. This invention provides such a new and useful system and method.

BRIEF DESCRIPTION OF THE FIGURES

FIGS. 5A-5D are exemplary result characterization report;

FIGS. 7A and 7B are schematic representations of a method applied to storing and querying biological sequence data;

FIG. 15 is a schematic representation of variation selecting a set of overlapping biological sequence k-mers.

DESCRIPTION OF THE EMBODIMENTS

Figure 1:
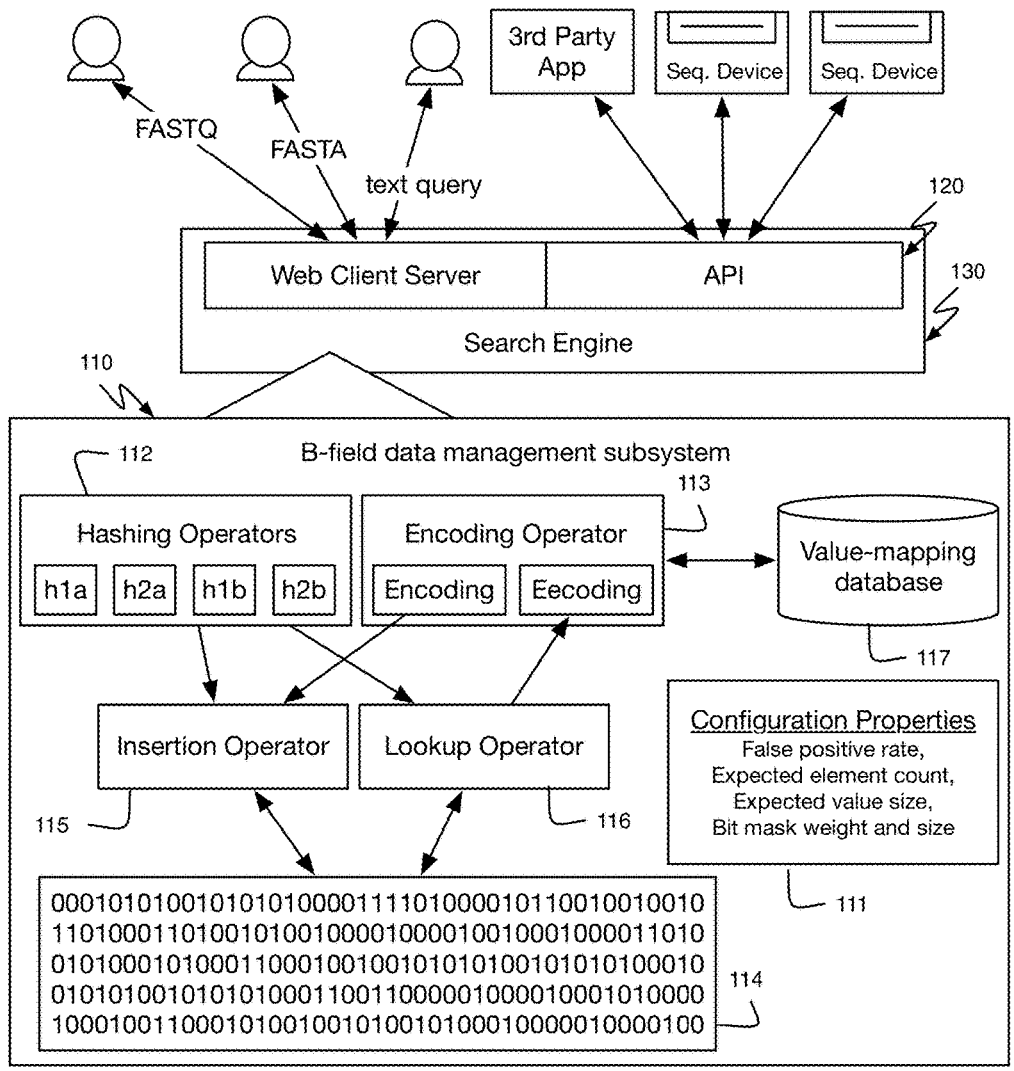
FIG. 1 is a schematic representation of a system of an embodiment.

The following description of embodiments of the invention is not intended to limit the invention to these embodiments but rather to enable a person skilled in the art to make and use the invention.

1. Summary

The system and method for characterizing biological sequence data through a probabilistic data structure of an embodiment functions to employ a probabilistic data structure to DNA sequence search and analysis. The probabilistic data structure used in the system and method and described herein is referred to as the B-field data structure. The B-field data structure is a space-efficient, probabilistic data structure for storing a set of x-y key-value pairs. B-fields support insertion (INSERT) and lookup (LOOKUP) operations, and share a number of mathematical and performance properties with the well-known probabilistic data structure the Bloom filters. In contrast to Bloom filters, which only support set membership queries, B-fields support associating a set of x, y key-value pairs, where S is the set of stored x values, $|S|=n$ D is the set of all possible y values ($f:S \to D$), and $\theta$ represents the "value range" of the B-field ($\max(D)=\theta$). Stated differently, if $f(x)=y$, D is the domain of the function $f(x)$. The B-field probabilistic data structure includes a set of potential advantages and benefits over alternative probabilistic and deterministic data structures for associating keys and values, such as space efficiency, speed, well-defined and bounded errors, and dynamism and mutability. Specifically, B-fields exhibit a number of key properties that no other single known data structure provides. The B-field properties can be particularly beneficial when applied to a biological sequence query use-case, which depends on large datasets and large sets of lookups. The system and method can store encoded representations of DNA sequence fragments (i.e., k-mers) in a B-field data array to determine set membership and value association.

The system and method leverage the properties of the B-field data structure. In operation, the system and method generally involve the insertion and lookup of key-value elements in a probabilistic data structure. The values are persevered during the insertion operations by encoding the values in a bit mask applied to a reference data array. More specifically, a B-field data management subsystem implements a B-field data structure by encoding a value (i.e., y) into a binary string and then inserting that binary string into a reference bit array at locations identified by k hash functions ($h_1, \ldots h_k$) for each inserted key (i.e., element x). When looking up a queried key, the B-field data management subsystem collects bit strings from a set of locations identified by k hash functions ($h_1, \ldots h_k$) of the queried key. The collected bit strings are bitwise ANDed to reduce the set into the original binary string, and the binary string is decoded into a value. There are numerous operational benefits to the system and method. When applied to biological sequence query and analysis, the system and method can yield results relatively quickly, such as three orders of magnitude faster than traditional methods (e.g., BLAST), or in approximately 0.05 seconds.

1.1 Space Efficiency

The B-field data structure can probabilistically store key-value pairs in a space-efficient manner for in-memory use. For many common use-cases or configurations, the B-field data structure can store billions of elements using only tens of gigabytes of storage (or a few bytes per key-value pair). Such space requirements can scale linearly with the number of elements in the B-field, n. Stated in an alternative manner, the B-field data structure has O(n) space complexity.

1.2 Speed

The B-field data structure can be substantially optimized for in-memory storage of key-value pairs and requires both relatively little computational overhead and few memory accesses. The INSERT and LOOKUP operations can exhibit O(1) time complexity, as can be seen below. In the problem area of biological sequence queries, a substantially large reference data structure incorporating billions of biological sequence data characterizations may therefore not suffer from the size of the reference data structure.

1.3 Well-Defined and Bounded Errors

Probabilistic key-value data structures can present numerous classes or types of errors, including false positives, indeterminacy, and erroneous retrieval. One implementation of the B-field data structure can constrain the types of errors to be defined and bounded. The erroneous retrieval error where a wrong value is returned for a given key can be avoided and prevented when properly implemented as a result of a property of the B-field data structure. Additionally, the indeterminacy error can be reduced or prevented.

A false positive error can be defined as the rate at which a data structure returns a value (y) when the key (x) does not exist in the set of stored x values (S). When x does not exist in S, the B-field data structure query operation should indicate x is out of range, such as by returning a special value $\perp$. B-field data structures exhibit false positives at an error rate of $\alpha$. At the cost of lesser space efficiency, $\alpha$ can be set to be arbitrarily small. Additionally, in the problem space of biological sequence queries, the query input (e.g., a sequence of DNA reads) may have sequencing errors at a rate such that false positive errors are not substantially detrimental to the overall objective of a particular query because sequencing errors are present in the query.

An indeterminacy error, denoted $\beta$, is the rate at which a data structure returns an indeterminate answer for $x \in S$, expressed either as a subset of D, which includes the true $y_i$ that is mapped to by the $x_i$ or an error. Intermediate components (e.g., individual B-field data arrays) of the B-field data structures can have $\beta$ errors, for a complete B-field data structure (with multiple B-field data arrays) $\beta=0$ or $\beta \approx 0$ as is described more below. The number of the B-field data arrays can be used to effectively control the indeterminacy error, including eliminating it altogether, depending on the sensitivity of a given application of the B-field data structure.

1.4 Dynamism & Mutability

As opposed to some other probabilistic data structures, B-field data structures can support dynamic sets where some or all $x \in S$ are unknown at the time the data structure is created. The B-field data structure can be used in a variety of real-time applications not supported by data structures limited to static sets (where all $x \in S$ must be known at the time the data structure was created).

1.5 Generalizability

One potential benefit of the B-field data structure is that the data structure can be highly generalizable to operate efficiently for small and large set sizes and small and large value ranges. For example, B-field implementations can store billions of keys across both small (e.g., $\theta \approx 10$) and large value ranges (e.g., $\theta \approx 2^{20}$). The B-field data structure can exhibit good performance properties for a $\theta$ as large as $2^{32}$.

The implementation of the B-field data structure can be hardware agnostic and can be tuned for specific close-to-the-silicon hardware configurations and/or can be generalized for portability across various computing platforms. In one variation, the B-field data structure can be used in commodity computing resources, such as those obtained from various distributed computing platform providers. The properties of the B-field data structure—when particularly applied to biological sequencing problems—can enable query services and near real-time response through a web platform. A web platform can be a network accessible service (e.g., via the internet, an internal network, or any suitable network). Additionally, the system and methods relating to applications of the B-field data structure can be applied to applications beyond biological sequence data. The systems and methods can be used in key-value insertion and search in the fields of DNS routing, service discovery, scientific computing, local data applications, and other suitable applications.

In an exemplary implementation, the system and method are applied within a biological sequence query service offered over the internet. The biological sequence query service can include a pre-populated reference data structure that stores billions of key-values defining associations of DNA read fragments and biological characterization. The reference data structure may be updated with new information periodically, such as based on new research or information obtained from queries.

A biological characterization can be any suitable associated information related to a sequence fragment such as a biological classification, trait properties, reference number, or any suitable information. In one variation, the biological characterization can be hierarchical biological classification. The biological classification can be rank-based (e.g., using kingdom, phylum, class, order, family, genus, species) or rankless. Such biological characterizations can be based on nucleotides or protein sequence data. The biological query service can receive full or partial DNA sequence data (such as FASTA or FASTQ files). A B-field lookup process can be performed for a set of fragments in the full or partial DNA sequence data to obtain a set of characterizations. From the set of characterizations, a characterization report can be generated, such as the characterization reports shown in FIGS. 5A-5D. Alternative use cases may use any suitable type of associated value for the characterization.

2. System for Characterizing Data: Probabilistic Data Structure

As shown in FIG. 1, the system for characterizing data through a probabilistic data structure functions to apply the B-field data structure to insertion and lookup of key-value stores in a reference data array. In particular, the system can resolve biological sequence data through a B-field data structure by inserting biological sequence data fragments with biological characterization and looking up characterization for a biological sequence data query. The system functions to transform encoded representations of physical biological properties into known identifying characterizations. The system can be applied to comparing primary biological sequence information, such as amino-acid sequences of different proteins or nucleotides of DNA sequences. Similarly, the system can additionally or alternatively be applied to RNA or other suitable biological sequence information. Herein, the system is primarily discussed as it applies to biological sequence information. However, the system is not limited to biological sequence applications and can alternatively be applied to other areas that include resolving key-value information.

The system can include a search engine platform that incorporates a B-field data management subsystem 110, a query interface 120, and a search engine 130. The system functions to use B-field data management subsystem 110 in providing a query service. The B-field data management subsystem 110 supports the underlying data transformation that is used in the application logic of the search engine 130 and expressed through the client interface of the query interface 120. The search engine platform as discussed can be focused on a particular class of queries such as biological sequence information. The search engine platform can include a network-accessible service, such as accessible over the internet, over an internal network, or over any other suitable network. Through the speed and memory efficiencies of the system and method, the search engine platform can be deployed to a distributed computing platform (e.g., a cloud hosting environment, a managed server, a virtual machine, and/or other commodity computing resource). The system of the search engine platform can depend on a centralized canonical cluster, but the system may alternatively be sharded, replicated, or otherwise distributed across multiple computing and/or regional environments. Alternatively, the search engine can include an on-premise or local search engine platform. For example, a sequencing device may have a local implementation of the system embedded into the device operating system and without any network connectivity.

The B-field data management subsystem 110 implements a B-field data structure by encoding a value (i.e., y) into a binary string and then inserting that binary string into a reference bit array at locations identified by k hash functions ($h_1, \ldots h_k$) for each inserted key (i.e., element x). The B-field data structure is designed for storing key-value pairs as opposed to set membership information. The B-field data management subsystem 110 can include the components used in a B-field data structure, which can include configuration parameters 111, key hashing operator 112, value encoding operator 113, a B-field reference data array 114, and insertion operator 115, lookup operator 116. The B-field data management subsystem 110 can additionally include a value-mapping database 117 when the value is used as an associated value that maps to high bit value information (e.g., images, long strings, characterization). The B-field data management subsystem 110 can manage insertion and lookup operations of key-value pairs in a B-field reference data array 113. The B-field data management subsystem 110 functions as a set of components used in processing B-field data structure related operations. The B-field data management subsystem 110 can include an input for issuing insertion and lookup commands. An insertion command can include a source key-value pair. The output of the B-field data management subsystem 110 for an insertion command can be the success or failure of the request. A lookup command can include the key to be looked up, and a response of the value can be returned. Alternatively, an associated value can be returned, which can then be used with the value-mapping database 117 to access the end value data. The search engine 130 can implement the B-field data management subsystem multiple times in generating a collective result to a query that requires multiple B-field data structure interactions.

The configuration parameters 111 function to set the performance and operational settings used in managing a B-field data structure. The configuration parameters 111 can be configured by the search engine platform operators such that the configuration is globally used in B-field data structure operations for search queries. Alternatively, configuration parameters 111 can be individually set for different segments of the search engine platform. For example, different types of search queries may be made against different instances of B-field data structures. In this example, different repositories of information may be inserted and queried in different instances of a B-field reference data array, and different configuration parameters 111 may be used for the different instances. The configuration properties can alternatively be set by an account or the user inserting and/or looking up information such that search engine performance can be tailored for specific use-cases.

Configurable parameters 111 can include a maximum false positive rate $\alpha$.

Configurable parameters 111 can include the expected number of values to be stored n where $n=|S|$. If more than n elements are inserted into the B-field, the expected false positive rate can exceed the desired maximum.

Configurable parameters 111 can include the maximum value $\theta$ of the set of all possible y values. Using the encoding technique for the value encoding operator described herein, D can include of all or a subset of the non-negative integers $\{1, \ldots, \theta\}$ or $\{0, \ldots, \theta-1\}$. The values can additionally be mapped to any set of up to $\theta$ distinct values by using y as an index or associated value referencing an end-value in a set D', where $|D'|=\theta$ (in which case y serves as an intermediate associated value). The value-mapping database 117 functions to provide the mapping between the y value and the end-value. The value-mapping database 117 can be used when the end-values of y are in a high bit-space, such as for y values including images, long strings, data objects, and/or other suitable values.

Additionally, the configurable parameters 111 can include a value v, and a value κ such that $$\binom{v}{\kappa} \geq \theta \text{ where } \binom{v}{\kappa}$$

is the combination formula:

$$\binom{v}{\kappa} \geq \frac{v!}{\kappa!(v-\kappa)!}.$$

In one variation, the B-field data management subsystem 110 encodes the values y in v-length bit strings with exactly κ ones (or a weight of κ in information theoretic terms). In this variation, κ and v are described as the bit mask weight and size, respectively. Accordingly, the B-field data management can minimize κ and keep v within an order of magnitude of κ when selecting v and κ. For example, in the exemplary situation of attempting to select v and κ such that $$\binom{v}{\kappa} \geq 1000,$$

v can be set to v=20, κ can be set to κ=3, and $$\left(\binom{v}{\kappa} = 1140\right)$$

instead of setting v=1000 and κ=1.

The key hashing operator 112 functions to convert a key parameter into a set of index values suitable for interacting the B-field data structure. The index values are used to identify array locations within the B-field reference data array where elements are inserted during an insert or accessed during a lookup. The index values can be integer values that exist in the space of 0 to approximately the size of the B-field reference data array. More specifically, the integer value space of the hashing functions can be 0 to the size of the reference data array instance minus the length of the fragment size v. The key hashing operator 112 can be a set of hash functions that are individually applied to the key of a key-value element.

The set of hash functions can include hash functions designed for pseudo-randomness and distribution qualities. In particular, the set of hash functions can include highly random (or pseudorandom) or "perfectly" random hash functions. However, the B-field data structure can alternatively use heuristic off-the-shelf hash functions in practice (such as the fast MurmurHash3 function). The set of hash functions is preferably fully independent. However, in one variation, using two or more independent hash functions as seeds and relaxing the independence requirements for the remaining hash functions can improve performance and simplify development and maintenance. For example, two hash functions $h_a(x)$ and $h_b(x)$ can be used to create n composite hash functions, with each hash function defined as $h_n(x)=h_a(x) \times ((n-1) \times h_b(x)))$. The set of hashing functions can be the same underlying hashing algorithm using a different seed. The number of hashing functions used can be configured according to preferences of performance of the B-field data structure. A hashing function can include a modulus operator to transform the set of hash output values to a defined range.

The value encoding operators 113 function to translate between a value and a bit pattern. The bit pattern can be used during key-value insertions where the bit pattern is bitwise ORed with different locations of the B-field reference data array as specified by the key hashing operators 113. The bit pattern is additionally encountered during a lookup of a key where different bit fragments from the B-field reference data array (as specified by the key hashing operators 113) are bitwise ANDed to result in a bit pattern decodable into the value associated with the queried key.

Figure 2:
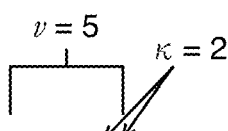
FIG. 2 is an exemplary representation of value encoding operators.

The encoding operators 113 can include an encode operation that translates a given y value into a binary v-length string with a κ ones suitable for insertion into the B-field reference data array. One encoding system involves translating y into the $y^{th}$ v-length κ-weight bitstring of all $$\binom{v}{\kappa}$$

combinations in lexicographic or reverse lexicographic order (e.g., 1 translates to "0001" if v=4 and κ=1 using a lexicographically ordered encoding scheme). Other even- and uneven-weighted codes can additionally or alternatively be implemented (e.g., error-correcting codes). As shown in FIG. 2, the ENCODE (and inverse DECODE) operators can be used to translate values 0-10 to associated bit patterns, where v=5 and =2.

The B-field reference data array 114 functions as a memory allocation that acts as a mechanism through which the key-value information can be stored in a relatively space efficient and easy to access format. The B-field reference data array 114 can be a bit array that contains a set of binary bits set to one or zero. Bits in the B-field reference data array can be stored in actual bit form (e.g., lowest form of binary memory storage) but can additionally include higher forms of memory storage where multiple physical bits are used to represent one bit-position of the bit array. Initially, the B-field reference data array 114 is zeroed. The B-field reference data array 114 can alternatively be set to all ones initially where the bitwise operators are adjusted appropriately. The B-field reference data array 114 can include a single bit array instance (i.e., $Array_0$), but additional secondary bit arrays can be implemented (i.e., $Array_2, \ldots, Array_a$) to manage indeterminacy error. The secondary bit arrays can be implemented in distinct memory arrays (e.g., distinct memory blocks or in different storage locations). Alternatively, a secondary bit array may be overlapping with a primary and/or other secondary bit arrays in which case a set of hash functions distinct from other bit arrays can be used for a secondary bit array. A B-field reference array 114 can be initially constructed by inserting the full set of key-value elements. However, the B-field reference array 114 can be a mutable data structure updated with key-value elements at a time instance distinct from the initial construction.

The size of the B-field reference data array 114 can scale linearly with the number of elements in the B-field n. During configuration, the size can be set according to the number of elements. The number of elements may be known or predicted. More specifically, a primary array is set to approximately the size of mκ-bit array. The size of the primary array can additionally be used in setting the number of hash functions, k. The configuration of the B-field data management subsystem 110 can use the equations:

$$m = -\frac{n \ln p}{(\ln 2)^2} \text{ and } k = \frac{m}{n} \ln 2$$

in setting m and k (distinct from κ), where p is the probability of a single-bit error. After having calculated m and selected κ, mκ-bit array of memory can be allocated and initialized. While multiple bit arrays can be used, the initial, primary array (i.e., $Array_0$) is preferably Mκ in size.

The B-field reference data array 114 can include a primary array and a set of secondary arrays. The secondary arrays include arrays that can be used subsequent to an initial array during insertion and lookup operations when an indeterminate error is encountered using the initial array. The indeterminate error β is the chance that a given value x∈S returns a v-length bit string with >κ bits flipped to 1 (at least κ bits are guaranteed to be set to 1 by the insertion operator 115). A cascading series of secondary arrays can reduce the indeterminate error rate, such as to zero or approximately zero.

The lookup operation of a B-field array can include a false positive (α) and indeterminacy (β) errors. Error rates can be derived based on the pattern of the insertion operation, which sets up to κ random bits within the bit array to one for each of k hash functions. In a real-life scenario, the pattern of zeros and ones may not be substantially random at low fill. As a first step, the probability that any single bit in the v-length bit string will be incorrect after the k bit strings are bitwise ANDed together (described here as p, the probability of a single bit error) can be determined. The probability that an individual bit is not set to one by a single hash function (each setting K bits) during the insertion of an $x_i$ is:

$$1 - \frac{\kappa}{m\kappa}.$$

Canceling the κ bits set by the hash function yields:

$$1 - \frac{1}{m}.$$

Then, the probability that a single bit is not set for any of the k hash functions is:

$$\left(1 - \frac{1}{m}\right)^k.$$

After n insertions of $x_1, \ldots, x_n$, the probability that a given bit remains zero is:

$$\left(1 - \frac{1}{m}\right)^{kn}.$$

After each of the k components of the lookup (one per hash function) the probability that an individual bit is wrongly a one is:

$$\left(1 - \left(1 - \frac{1}{m}\right)^{kn}\right)^k \approx (1 - e^{kn/m})^k.$$

Substituting the formulas for optimal m and k values from above yields:

$$p = (1 - e^{-(m/n \ln 2)n/m})^{(m/n \ln 2)},$$

where p is the probability that a given bit in the v-bit string encoding a given value $y_i$ is a one when the bit should be a zero. Since a false positive can be experienced when there are ≥κ bits incorrectly flipped to one in the v-bit string, α is a CumBinom(v,κ,p) where CumBinom is the right tail of the cumulative binomial distribution:

$$\alpha = Pr(X \geq \kappa) = \sum_{i=\kappa}^{v} \binom{v}{i} p^i (1-p)^{v-i}.$$

Correspondingly, β is the chance that a given value x∈S returns a v-length bit string with >κ bits flipped to one (at least κ bits are guaranteed to be set to one by the INSERT operation). This corresponds to CumBinom(v−κ,1,p). Without correction, β may be too high for many use-cases, and the use of cascading secondary arrays can thus be used to apply a correction to β such that effectively β≈0. This can additionally have the effect of reducing α from the cumulative binomial distribution for all values ≥κ to the binomial distribution for κ exactly, which is $$\binom{v}{\kappa} p^\kappa (1-p)^{v-\kappa}.$$

Some use-cases may alternatively be suitable with the β present with only a primary array.

In order to eliminate or otherwise reduce β errors (and, as a side effect, to reduce the magnitude of false positive errors), a key-value insertion log can be maintained. For each key-value inserted, a record of the key-value is logged. The key-value insertion log can be used in checking for indeterminacy errors. Alternatively, indeterminacy errors can be checked subsequent to insertion to avoid storing the key-value. The record log can additionally be used in reproducing the B-field reference data array. The key-value insertion of the input keys $x_1, \ldots, x_n$ are iterated through a second time. Instead of inserting the input keys into the primary array, a lookup is performed and the number of one bits in the v-bit string, or $b_i$, is noted for each $x_i$. If $b_i > \kappa$, a β-class error occurred as a known x∈S is not returning its corresponding v-length κ-weight bit string. The subset of $x_1 \ldots x_n$ for which $b_i > \kappa$ (which has an unexpected number of elements βn) is then inserted into a second array $Array_1$, which is created following the above procedures except that the subset is scaled to be a βmκ-bit array as because the subset has only βn elements rather than n elements.

Implementation of one or more secondary arrays allows for an indeterminate lookup query of x against $array_0$ yielding >κ one bits to then be checked against $Array_1$ as well. Since the probability of $x_i$ yielding >κ one bits is β for $Array_0$ and also β for $Array_1$ (which can share identical properties but contain a smaller number of elements), the indeterminacy rate is reduced from β to $β^2$ with the addition of $Array_1$. Further arrays $Array_2 \ldots Array_{a-1}$ can be added until a set of a arrays is formed, choosing a such that $β^a n < 1$ (for the case of β is zero) or that a is suitably small. Continuing from above, if $array_1$ yields an indeterminate lookup query, the subsequent array (e.g., $Array_2$) can be checked until a value is determined or the secondary arrays are exhausted. In various implementations, a value of a between two and five can be sufficient where few elements are in the final $Array_{a-1}$ even if n is large.

The secondary arrays can additionally function to lower the false positive rate α. Because a false positive where $x_i \notin S$ yielding >κ one bits also leads to a check against $Array_1$ (and $Array_2, \ldots, Array_{a-1}$ if the lookup operation yields >κ one bits in $Array_1$ and subsequent secondary arrays), the false positive rate α is also reduced from the cumulative binomial distribution toward the binomial $$\binom{v}{\kappa} p^\kappa (1-p)^{v-\kappa}.$$

Specifically, the secondary arrays can reduce the set of circumstances where α errors can occur from anytime ≥κ one bits are flipped for an $x_i \notin S$ to two cases, including: 1)

when exactly κ one bits in Array$_0$ are flipped for an $x_i \notin S$ (the binomial); and 2) a relatively rare case where >κ one bits are flipped in Array$_0$ ... Array$_{a-2}$ and exactly κ bits are flipped in the final Array$_{a-1}$. The probability of this second case is approximately zero as the chance of >κ bits flipping decreases exponentially in subsequent secondary arrays.

Relating to the set of data arrays, a cascade of secondary arrays beyond the primary array can reduce the false positive rate α from a cumulative binomial distribution to the binomial for κ individual bit-level errors and eliminates (substantially) all indeterminacy errors (i.e., β=0). Such error reduction can be achieved at a relatively modest cost to the space efficiency of the B-field. Array$_0$ requires $β^0$mκ bits, while Array$_1$ requires $β^1$mκ bits. Dividing everything by Mκ bits reveals the underlying geometric series of $1+β^1+ \ldots +β^{α-1}$. The sum of which is:

$$\frac{1}{1-β}.$$

The total memory area required by the B-field with a primary Array$_0$ and α−1 secondary arrays is only $$\frac{1}{1-β}mκ \text{ bits.}$$

In some use-cases, an initial indeterminacy rate of 0.05≤β≤0.20 may be common. Correcting this for a $$5\% \left(\frac{1}{0.95}\right) \text{ or } 25\% \left(\frac{1}{0.80}\right)$$

spaced penalty can be achieved, but a B-field can be constructed with only an Array$_0$ at the cost of needing to manage β indeterminacy errors in the key-value lookups.

Configuration of the B-field reference data array 114 can vary in numerous ways from the variations described herein. In some situations, β can be set to a small non-negative value proportional to α to constrain the number of required arrays a.

The insertion operator 115 functions to add a key-value element to the B-field reference data array 114. The insertion operator 115 includes a hashing stage, an encoding stage, and bitwise insertion stage. The insertion operator 115 applies the key hashing operator 112 to a key of the key-value element. A set of indexes is the output of the hashing stage. The value encoding operators 113 are then applied to the value of the key-value element. A given value y is translated into a binary v-length string with κ ones suitable for insertion into the B-field reference data array 114. According to a standard encoding system, such insertion can involve translating y into the $y^{th}$ v-length κ-weight bit mask of all $$\binom{v}{κ}$$

combinations in lexicographic or reverse lexicographic order (e.g., 1 translates to "00011" if v=5 and κ=2 using a lexicographically ordered encoding scheme), as shown in FIG. 2. The insertion operator 115 can also implement other even- and uneven-weighted codes can, such as error-correcting codes. In one variation, an initial value can be directly encoded to a bit mask/bit string. In another variation, the initial value is stored in a value-mapping database indexed by an identifying value. The identifying value can be an integer encoded into the bit mask.

Figure 3:
FIG. 3 is a schematic representation of an exemplary insertion.
Figure 3:

The bitwise insertion stage sets bits in the B-field reference array 114 by bitwise ORing the bit mask at each location specified by the set of indexes, which functions to place the encoded value y into the B-field reference array 114. The indexes from the k hash functions ($h_1(x) \ldots h_k(x)$) can be mod'ed with mod mκ (where mod x is the remainder of a value divided by x). The resulting values are indexes for the bitwise OR insertion of the encoded value y, wherein the first bit of the v-length bit mask is mod mκ (h(x)) and the last bit is mod mκ (h(x))+v−1. In an exemplary case of inserting the first x-y key-value element into an Array$_0$ where k=5, v=6, κ=1, and y=1, the insertion operator 115 bitwise ORs the bit mask 000001 into the mκ-bit array 5 times and changes a total of 5 bits from 0 to 1. As shown in FIG. 3, a sample insert operation for a key-value pair where $y_i$=2 and the B-field is configured with k=6, v=5, κ=2 updates the bit array in 6 locations with the bit mask of "00101". The insertion operator 115 can be used in primary arrays or secondary arrays.

The lookup operator 116 functions to determine, isolate, or search for a value based on a key query. The lookup operator 116 can mirror the insertion operator 115. The lookup operator 116 implements hashing operators to identify positions in the B-field reference array 114 and then applies bitwise operations to a set of bit strings collected at each of the identified positions. The lookup operator 116 can thus output an encoded value, which can be decoded to access a corresponding end value. Accordingly, the lookup operator 116 executes a hashing stage, an accessing stage, a bitwise operation stage, and a decoding stage.

Figure 4:
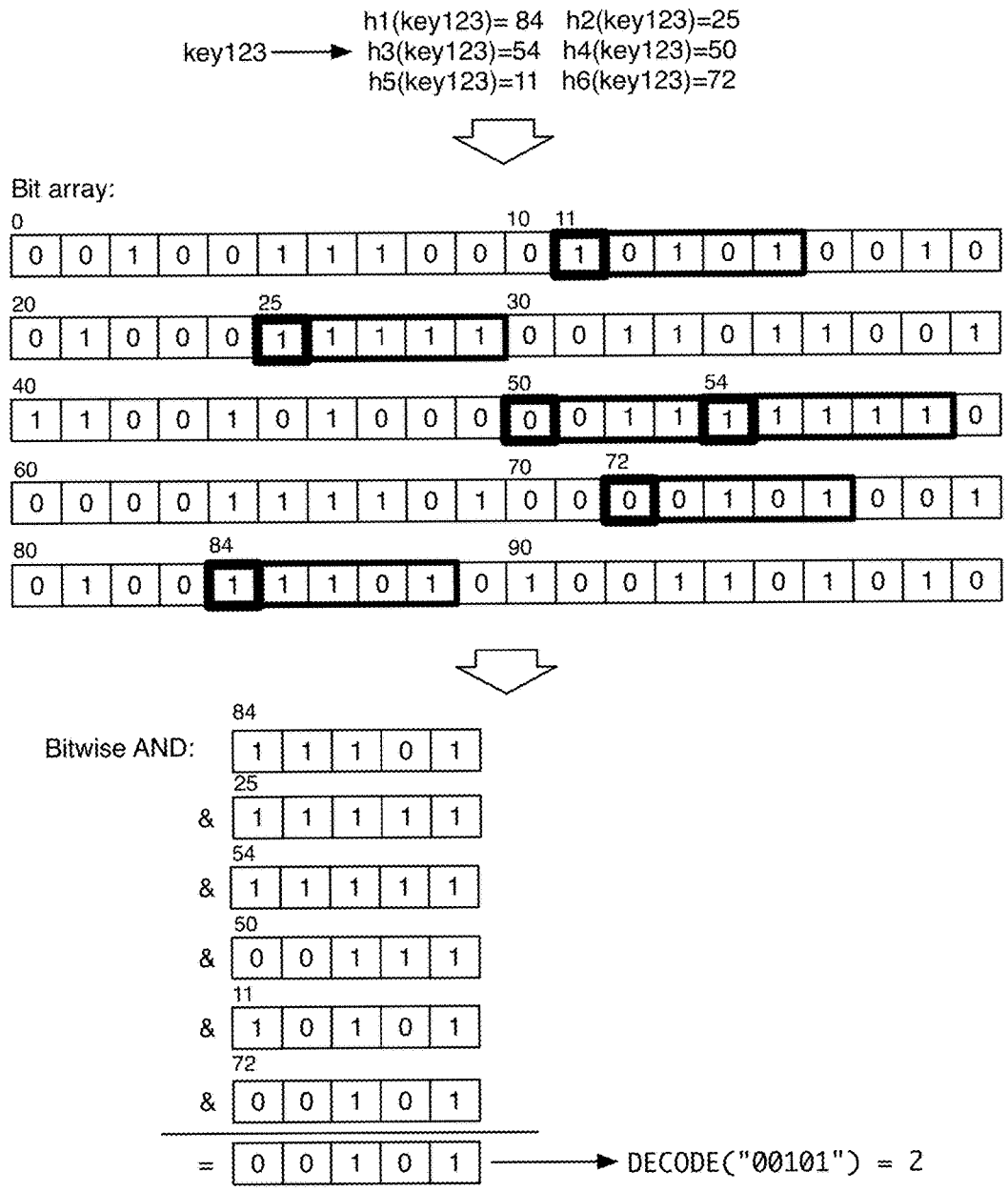
FIG. 4 is a schematic representation of an exemplary lookup.

More specifically, a given $x_i$ selected for lookup in the B-field reference array 114 is hashed k times using the hash functions $h_1 \ldots h_k$ (all mod mκ). At each index position for $h_1 \ldots h_x$ a v-length bit string is taken and bitwise ANDed with an initial v-length bit string including κ1s (i.e., having a weight of κ). Using the values from the prior example, if the following five 6-bit strings {111011, 111111, 100001, 100011, 110011} are found in the B-field Array$_0$ at $h_1(x_i) \ldots h_k(x_i)$, the bitwise AND of these returns 000001, which can be decoded to yield the value 1 for $y_i$. As shown in FIG. 4, a sample lookup operator process, where the value $y_i$=2 associated with a given $x_i$, retrieves $v_i$ from a B-field where v=5, κ=2, and k=6.

Looking across various (e.g., all) possible cases, if the resulting bit string has fewer than κ ones, then $x \notin S$ and the B-field returns the special value ⊥ (as at least κ ones result from the insertion operator 115). If the resulting bit string has exactly κ ones, then the bit string is decoded using the decode operator (simply the inverse of encode operator) and the value $y_i$ mapping to the key xi is returned. This operation may erroneously return a $y_i$ for a $x \notin S$ at the false positive rate of α. And, finally, with a probability of β an indeterminate result with more than κ ones will be returned. Employment of subsequent B-field arrays can reduce β in this case.

The query interface 120 functions to obtain a key to query in the B-field reference array. The query interface 120 can be a graphical user interface. In one variation, a user can upload a biological sequence file, as shown in FIG. 15. The file may be in a common biological sequence format (e.g., FASTA, FASTQ files) and/or of any other suitable file format. In another variation, the query interface 120 includes a text input field where biological sequence data can be entered directly. In yet another variation, the query interface 120 additionally or alternatively includes an application programming interface, a sequencing machine interface, or any other suitable type of query interface.

The search engine 130 functions to apply a search application logic to input data to produce a desired output. In one embodiment of searching biological encoding, the search engine applies the B-field lookup process for a moving window of sequence data. A set of biological sequence k-mers from a biological sequence sample can be processed to generate a set of resulting characterizations. The term k-mer refers to a set of possible substrings, of fixed length k, that are contained in a string. In computational genomics, k-mers refer to all the possible subsequences (of length k) from a read obtained through DNA Sequencing (note, k of k-mer is distinct from k used in reference to the set of hash functions). A characterization report can be generated from the set of resulting characterizations, such as those shown in FIGS. 5A-5D.

3. Method for Characterizing Data: Probabilistic Data Structure

Figure 6:
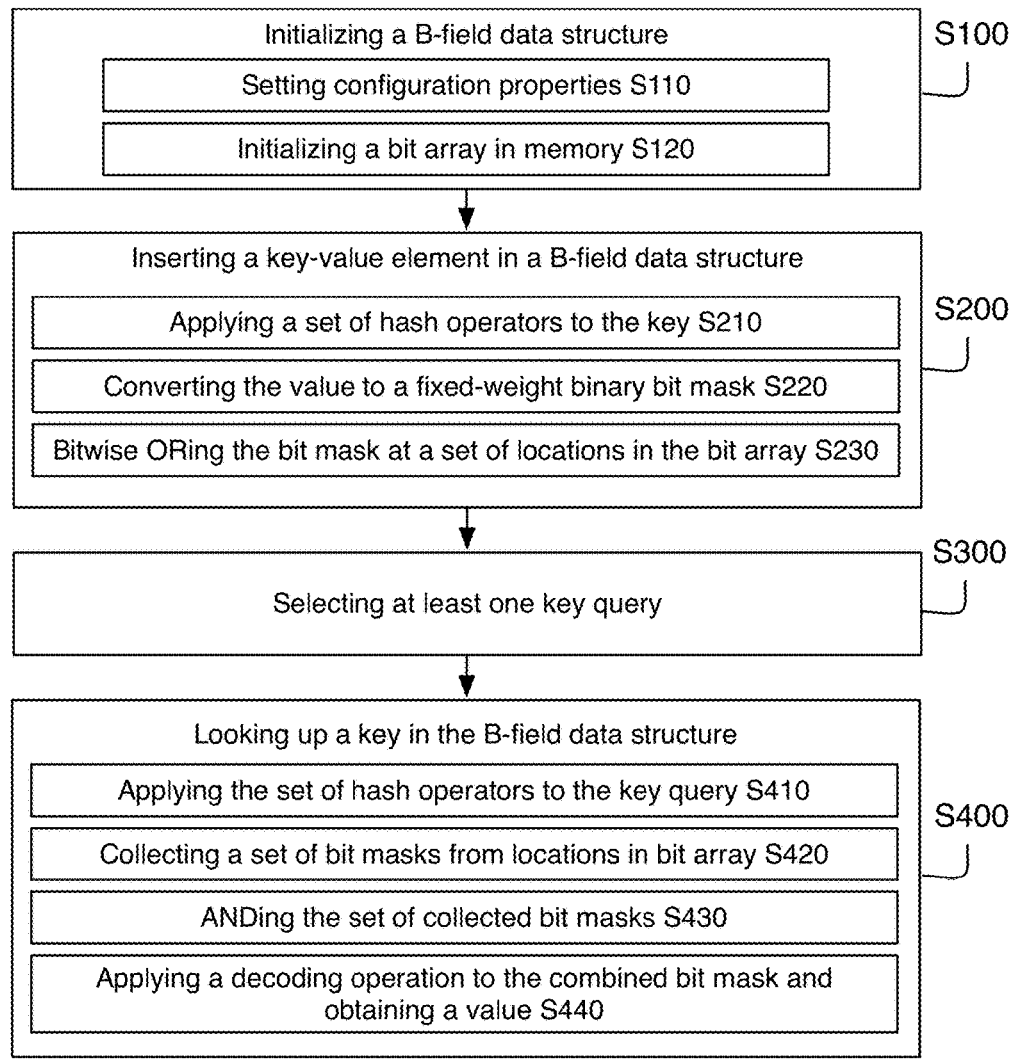
FIG. 6 is a flowchart representation of a method of an embodiment.

As shown in FIG. 6, a method for characterizing data through a probabilistic data structure can include initializing a B-field data structure in Block S100, inserting a key-value element into the B-field data structure in Block S200, selecting at least one key query in Block S300, and looking up a value of a key lookup request through the B-field data structure in Block S400. The method of one embodiment can be implemented to resolve biological sequence reads through a B-field data structure, such as by inserting biological sequence data fragments with a biological characterization and looking up a characterization for a biological sequence data query. The method functions to transform encoded representations of physical biological properties (e.g., DNA sequence data) into an identifying characterization based on a repository of pre-classified biological sequence analysis.

In biological sequence data applications, the key-value elements can be biological sequence keys mapped to characterization values. A biological sequence key can include a segment or subsection of a biological sequence read. For a DNA sample of ten base-pair length (a "10-length DNA sample"), the biological sequence may be "ACGTG-CACTC" (SEQ ID NO: 1). A biological fragment (or a biological sequence k-mer in the field of bioinformatics) can be set to any suitable length. As in the example above, a 6-length fragment or 6-mer of DNA sample may be "ACGTGC". The term k-mer refers to a set of possible substrings, of fixed length k, that are contained in a string. In computational genomics, k-mers refer to all the possible subsequences (of length k) from a read obtained through DNA sequencing.

Figure 5D:
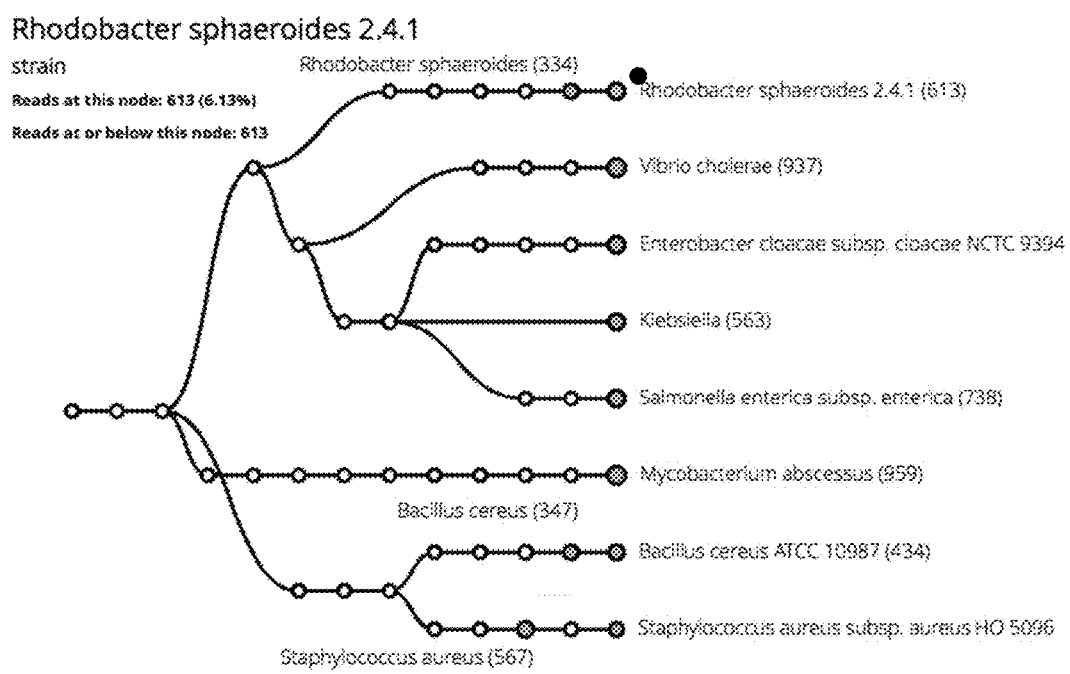

The characterizations can be biological characterizations, and, more specifically, the characterizations can be hierarchically ordered biological classifications, such as the classifications shown in FIG. 5D. The method can be implemented to compare primary biological sequence information, such as amino-acid sequences of different proteins or nucleotides of DNA sequences. Similarly, the method can additionally or alternatively be applied to RNA or other suitable biological sequence information.

Herein, the method is primarily described as it applies to biological sequence information. However, the method is not limited to biological sequence applications and can additionally or alternatively be applied to other areas, such as other areas necessitating resolution of key-value information.

The method can be applied to the system described above in managing and using a B-field data structure in key-value operations. The operational properties of the B-field data structure can facilitate performing the method in a variety of computing environments. In one implementation, the method hosts the associated data structures in an internet-accessible distributed computing environment. Additionally, inserting key-value elements and looking up key-value elements can similarly be performed within the distributed computing environment. In some cases, such "cloud" computing environments can be supported on commodity servers and hardware, which can be sufficient to implement the method. Additionally, the method can include sharding, replicating, or otherwise distributing a B-field data structure across multiple computing resources and/or regional environments, which can be used in scaling capacity of a query platform. Alternatively, the method can be implemented on-premise or locally on-device. For example, a sequencing device can perform a local implementation of the method on the device to provide automatic characterization information without network connectivity.

The method applies the B-field data structure described above. As described herein the method includes processes of the B-field data structure as the processes are applied to a bit array. A bit array can include any data storage construct used in storing sequential binary data. The bit array (more specifically a primary or secondary array) can consume a contiguous region of memory. The bit array can alternatively be partitioned between different memory locations and/or types of memory.

Figure 7A:
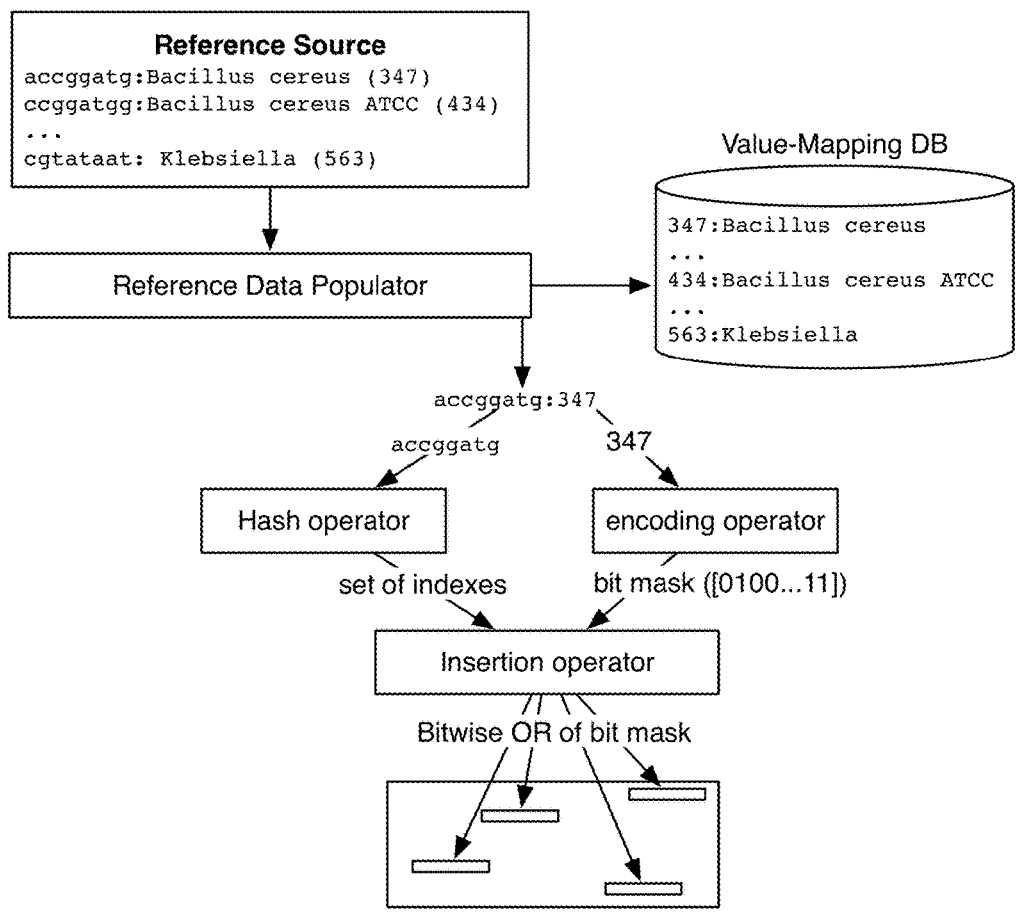

As shown in FIGS. 7A and 7B, an embodiment of the method for storing and querying a biological sequence sample can include: initializing a bit array in memory of a computing platform; inserting a set of reference key-value elements in the bit array, wherein a reference key-value element maps a biological sequence fragment key to a characterization; selecting a biological sequence query key; and extracting a characterization of the biological sequence query key from the bit array. Inserting a key-value element can include: obtaining a set of indexes by applying a set of hash operators to the biological sequence fragment key; converting the characterization value to a fix-weight binary bit mask through an encoding operation; and bitwise ORing the binary bit mask at a set of locations of the bit array where the set of locations is based on the set of indexes. Looking up the biological sequence query, as described below, can include: obtaining a second set of query indexes by applying the set of hash operators to the biological sequence fragment query key; collecting a set of bit masks from locations of the bit array based on the second set of query indexes; bitwise ANDing the set of bit masks into a combined bit mask; and applying a decoding operation to the combined bit mask and obtaining a characterization value of the biological sequence query key.

Additionally, the method can include applying a set of secondary bit arrays during insertion and/or look up of key-value elements, which can function to decrease at least the indeterminacy error. The method can also include accounting for key compression during inserting and/or looking up key-value elements, which can function to further reduce the space requirements to store the set of key-value elements in the B-field data structure. The method can alternatively include any suitable sub-combination of the variations described herein, such as a method specifically for forming a reference B-field data structure by inserting a set of key-value elements or a method specifically for looking up at least one key-value element through a B-field data structure.

3.1 Initialization Process

Block S100, which includes initializing a B-field data, functions to set up the B-field data structure and operators used in interacting with the B-field data structure. The initialization of the B-field data structure can enable the method to be customized to various use-cases depending on performance requirements such as error rates, space requirements, key-value element ranges, and other suitable properties.

Initializing a B-field data structure in Block S100 can additionally include setting configuration properties in Block S110. Setting configuration properties in Block S110 can further include setting properties of the bit array, insertion operators and lookup operators.

Setting properties of the bit array, insertion operators and lookup operators can include setting a desired maximum false positive rate.

Setting properties of the bit array can include setting an expected number of values to be stored, n. The expected false positive rate can be exceeded when more than the expected number of values is stored.

Setting properties of the bit array can include setting the maximum value of all the set of possible y values, $\theta$. In an encoding system, the set of possible y values D can be $\{1, \ldots, \theta\}$ or $\{0, \ldots, \theta-1\}$. This set of possible y values can be mapped to any set of up to $\theta$ distinct values by using y as an index to or associated value referencing an end value in a set D', where $|D'|=\theta$. This level of indirection of the value stored in the bit array can be applied when the end value is of a high value space, such as images or long strings. In this variation, Block S200 can include storing an identifier value to end value mapping in a database. For example, a database can store biological characterization information in an indexed database, and an integer identifier of the biological characterization information is the intermediate value stored through the bit array, as shown in FIGS. 7A and 7B.

Additionally, setting properties of the insertion operator and lookup operators can include setting the combinatorial properties of the bit masks. The settings of the combinatorial properties of the bit masks include the bit mask weight ($\kappa$) and bit mask length (v). The bit mask weight is the number of activated bits in a bit mask (e.g., number of ones in a bit string). The bit mask weight and bit mask length can be selected such that $$\binom{v}{\kappa} \geq \theta \text{ where } \binom{v}{\kappa}$$

is the combination formula. The bit mask weight can be minimized while keeping the bit mask weight within an order of magnitude of the bit mask length. For example, in the exemplary situation of attempting to select v and $\kappa$ such that $$\binom{v}{\kappa} \geq 1000,$$

v can be set to v=20, $\kappa$ can be set to $\kappa$=3, and $$\left(\binom{v}{\kappa} = 1140\right)$$

rather than setting v=1000 and $\kappa$=1.

Additionally, initializing a B-field data structure in Block S100 can include initializing a bit array in memory in Block S120, which functions to setup the bit array for use as a B-field data structure. Initializing a bit array can include allocating memory and setting the bit values of the bit array to an inactive setting. In one implementation and as described herein, bit values are set to zero in the inactive setting and are set to one when activated. An alternative approach can initialize the bit values to ones and then activate bits to zeros, and complimentary bitwise logic in other operations can be applied, such as by ANDing in place of ORing when inserting key-value elements. The method can also handle a set of bit arrays including a primary bit array and a set of secondary arrays. The primary array can be sized to MK bits.

3.2 Insert Process

Block S200, which includes inserting a key-value element into the B-field data structure, functions to perform an insertion process of a B-field data structure on the bit array. The insertion process is a probabilistic data structure insertion process that functions to enable key-value retrieval. Block S200 can implement a set of hashing operators to determine bit array insertion locations and an encoding operator to translate the value into a bit mask format for setting the locations of operation within the bit array.

Inserting a key-value element can include: obtaining a set of indexes by applying a set of hash operators to the key in Block S210; converting the value to a binary bit mask through an encoding operation in Block S220; and bitwise ORing the binary bit mask at a set of locations of the bit array where the set of locations are based on the set of indexes in Block S230. When the value of the key-value element is in a high value space, an identifier value is assigned to the end value. The method can include storing an identifier value to a characterization mapping in a database in Block S240, where the identifier value is used in place of the end value during bit array insertion operations. In one variation, the identifier value is an integer value incrementally greater than the previously used identifier value. The identifier value is used as an associated value referencing the end value stored in a database.

Block S210, which includes obtaining a set of indexes by applying a set of hash operators to key, functions to calculate a set number of key property hashes. The key can be a biological sequence fragment. The hash function can be substantially random, but may alternatively include a pseudo random algorithm. The hash functions are preferably fully independent. However, in one variation, two or more independent hash functions are used as seeds and the independence requirements for the remaining hash functions are relaxed. For example, two hash functions $h_a(x)$ and $h_b(x)$ can be used to create n composite hash functions, with each hash function defined as $h_n(x)=h_a(x) \times ((n-1) \times h_b(x))$.

A hashing function can be used on a variety of key properties. For example, the hashing function can be used in transforming a biological sequence k-mer into an index value. An index value can identify a bit location where a bit mask is applied to the bit array. In one variation, the maximum index value is based on the size of the bit array minus the size of the bit mask (e.g., a bit mask could not be fully added to the bit array if the index value was the last bit of the bit mask). Alternatively modulus operators or other approaches may be used to enable the index value to appropriately identify a suitable position in the bit array. Using the nomenclature introduced herein, k hash functions are applied to x (e.g., $h_1(x) \ldots h_k(x)$) and the mod(mk) of each value taken (where mod(x) is the remainder of a value divided by x).

Block S220, which includes converting the value to a binary bit mask through an encoding operation, functions to translate a value into a binary bit pattern representing the value. The binary bit mask can be fixed weight. The value can be a characterization value. However, the value can additionally be an identifying value that is a reference to a characterization value. The binary bit mask is a bit string with a fixed width (i.e., the bit mask length) and a fixed number of activated bits (i.e., the bit mask weight). Any suitable encoding pattern or heuristic may be used. In one variation, the method implements a systematic enumeration of bit combinations, as shown in FIG. 2. The encoding process can calculate the bitmask associated with the value. However, in another variation, the method can use a lookup table of pre-calculated associations of values to bit masks or use any suitable calculation process. The encoding process can be reversible by a decoding process, as in Block S400. The encoding operation and decoding operation are complimentary operations that translate between an integer value and a value associated bit pattern of a set size and set number of activated bits.

Block S230, which includes bitwise ORing the binary bit mask at a set of locations of the bit array where the set of locations are based on the set of indexes, functions to use the bit mask to activate (i.e., flips) bits at different positions in the bit array. Bitwise ORing the binary bit mask activates each bit where the bit mask is applied. As an example, the indexes obtained in Block S210 are 5, 30, and 102, and the bit mask is "101000". After ORing the binary bit mask at the set of locations of the bit array as indicated by the indexes at least bits 5 and 7, 30 and 32, and 102 and 104 are activated in the bit array.

Areas in the bit array where an encoded value was inserted for a key-value can be subject to multiple bit masking operations during other key-value insertions such that some or all of the bits of a particular section may be perturbed from the original state. Similarly, the portion of the bit array where a bit mask is applied may have previously been mutated by earlier key-value insertions.

The B-field data structure can be mutable such that key-value elements can be added at different times. In one variation, a set of reference key-value elements is inserted in a first time instance. Then, at a second time instance, a second set of key-value elements is inserted. For example, a biological sequence query platform can populate a B-field data structure with a biological sequence k-mer characterization key-values from a known repository such as RefSeq Release 65 from May 12, 2014, which can include sequence data on 2718 bacterial genomes and 2318 viral genomes, or genomes from the NCBI repository. Then after prolonged use of the B-field data structure in the biological sequence query platform, new genomic information is obtained from an outside source or through use of the query platform. The new genomic information can be inserted as key-value elements.

3.3 Lookup Process

A lookup operation will lookup the end value associated with a key. In the biological sequence information application, a biological sequence k-mer (i.e., a fragment or section of a biological sequence) can be queried and a characterization returned. In some cases, an error may be encountered, such as an indeterminate error. As described below, a full biological sequence search can involve a series of lookup operations, wherein individual results are combined into a result summary.

Block S300, which includes selecting at least one key query, functions to identify a key to be queried through the bit array. In one variation, a single key is looked up, and the corresponding value is returned. The key can be received through a query user interface, selected from a reference file, or received in any suitable manner.

Block S400, which includes looking up a value of a key query through the B-field data structure, functions to extract a value of the key query from the bit. Extracting the value includes isolating corresponding portions of the B-field data structure (in a primary bit array or a secondary bit array). A value extracted during a lookup process can be referred to as a result value. One result value can be returned for each key query. The hashing operations of the key allows multiple portions to be analyzed as a group to isolate the bits in common, which, when the result value is not indeterminate, results in an encoded value. The encoded value can preferably be decoded into a result value associated with the key. However, a false positive error can be a result in some situations. Looking up a value of a key query in Block S400 can include: obtaining a second set of query indexes through applying the set of hash operators to the key query in Block S410; collecting a set of bit masks from locations of the bit array based on the second set of query indexes in Block S420; bitwise ANDing the set of bit masks into a combined bit mask in Block S430; and applying a decoding operation to the combined bit mask to obtain a value in Block S440.

Block S410, which includes obtaining a second set of query indexes through applying the set of hash operators to the key query, functions to identify the bit array locations associated with the queried key. The set of hash operators can be the same set of hash operators used for insertions into the bit array as described in Block S210. The set of hash operators can change when performing an insertion or lookup in a secondary array.

Block S420, which includes collecting a set of bit masks from locations of the bit array based on the second set of query indexes, functions to access the segments of the bit array at the locations indicated by the indexes. For each of the index values, a bit mask is read from the bit array. In one example, the index values are 5, 30, and 102. If the bit mask length is set to six, then bits 5-10 form a first bit mask, bits 30-35 form a second bit mask, and bits 102-107 form a third bit mask.

Block S430, which includes bitwise ANDing the set of bit masks into a combined bit mask, functions to identify the common activated bits of the set of bit masks. In the case where no errors are encountered the result of the bitwise AND is the bit mask generated in Block S220. As the weight of the bit mask from Block S220 can be constant, the number of activated bits (i.e., bits in the default implementation) can be constant for successful lookups. False positive errors can occur when ≥κ activated bits are found, and indeterminate errors can be present when >κ activated bits are found. Secondary arrays can be similarly implemented to reduce such errors.

Block S440, which includes applying a decoding operation to the combined bit mask and obtaining a value, functions to translate the combined bit mask into a value.

The decoding operation can be complimentary to the encoding operation. In one variation in which a lookup table is implemented, the same row is accessed as during the encoding process. With the use of a value-mapping database, decoding translates the combined bit mask into an identifying value. In this variation, the method includes accessing an end value associated with the identifier value in the database. The identifying value is then used to access the end value stored in the value-mapping database. For example, the combined bit mask can be decoded into an identifier value. The identifier value can then be used to access a characterization value stored in a database. The end result value can be the value associated with the key when the key-value pair was inserted into the B-field data structure. In the use-case of querying a biological sequence k-mer, the result value can be a characterization associated with that specific k-mer.

3.4 Multiple Array Process

Figure 8A:
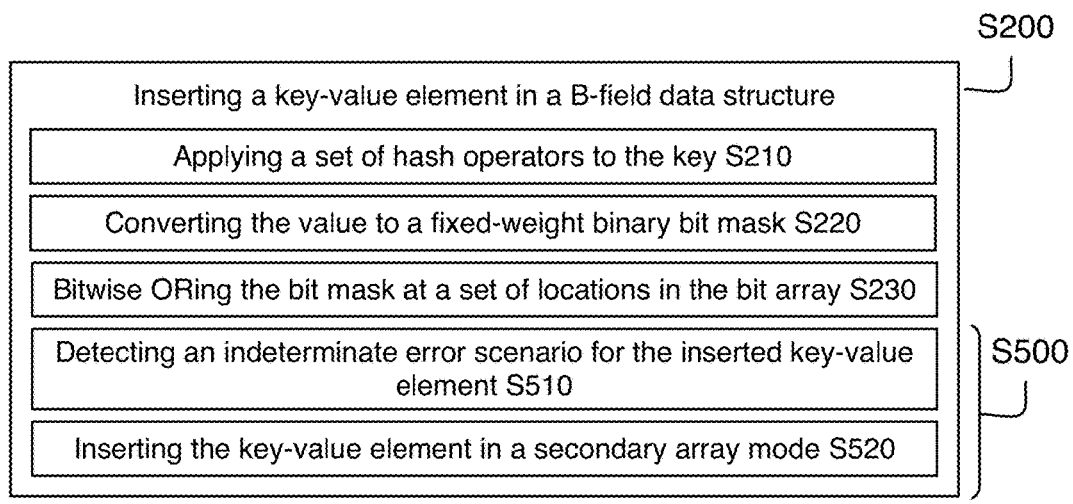
FIGS. 8A and 8B are detailed flowchart representations of a variation employing secondary bit arrays.
Figure 8B:
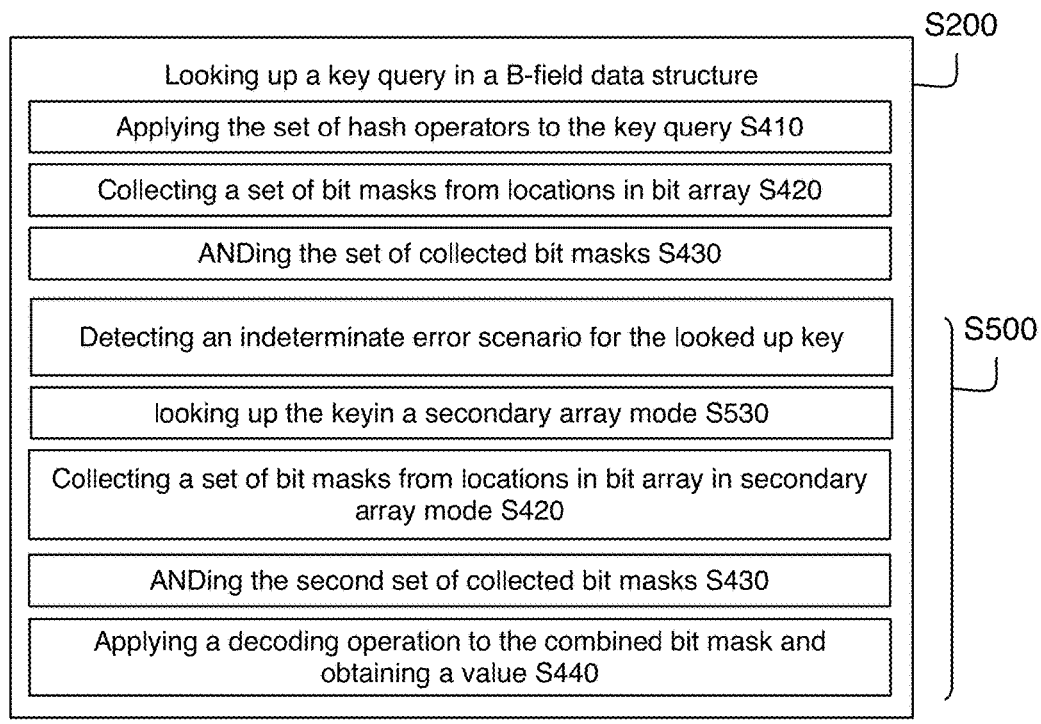

As shown in FIGS. 8A and 8B, an additional variation of the method can include employing secondary bit arrays in Block S500, which functions to eliminate or reduce indeterminacy errors and reduce false positives. As the B-field data structure defines a probabilistic data structure, storing a key-value element in two different bit arrays with different bit array sizes, hashing operators, set membership, bit mask properties, or other suitable configuration differences can result in different error occurrences. When an error is encountered in a primary bit array, the error may not be present when stored in a secondary bit array mode. For example, when elements $x_1$, $x_2$, and $x_3$ are stored in bit Array$_1$ there could be the situation where the activated bits happen to align so that a lookup of $x_1$ is an indeterminate error (the combined bit mask has more activated bits than the bit mask weight). During insertion, the error event may be detected and $x_1$ thus inserted into bit Array$_2$. In this example, because $x_1$ is the only element in bit Array$_2$, the indeterminate error does not occur. A cascading set of secondary arrays can be used to further reduce error rate of the method.

Employing secondary bit arrays in Block S500 can include detecting an indeterminate error scenario of the bit array for an inserted key-value element in Block S510, inserting the inserted key-value element in a secondary array mode in Block S520; looking up a key in a secondary array mode in Block S530.

Figure 11:
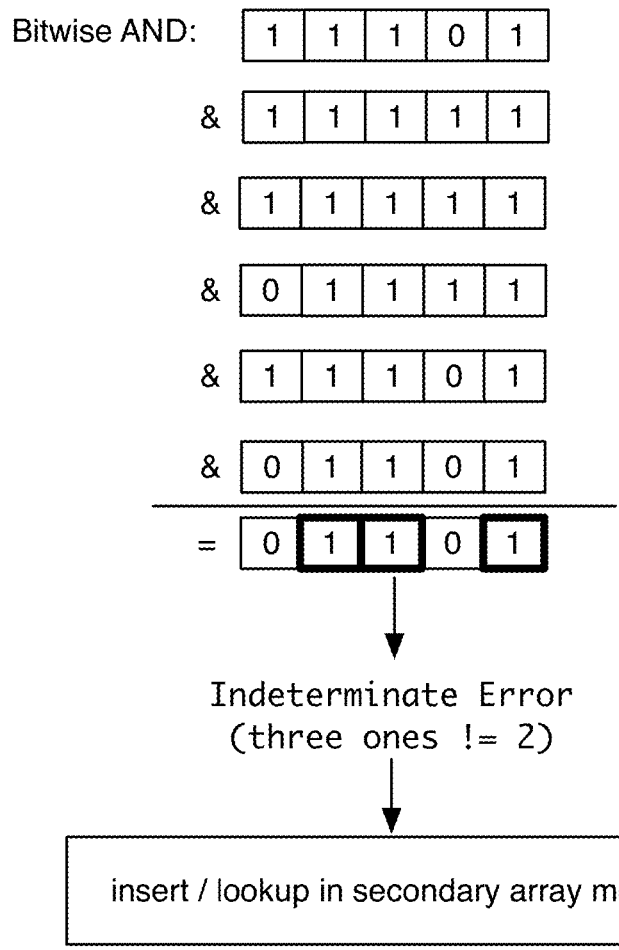
FIG. 11 is a schematic representation of detecting an indeterminate error scenario during a insertion or lookup.

Block S510, which includes detecting an indeterminate error scenario of the bit array for an inserted key-value element in Block S510, functions to determine when a secondary array mode should be used. A secondary bit array can be selectively applied to handle detected errors. An error occurrence is detected when a key-value element is inserted, resulting in an indeterminacy error, as shown in FIG. 11. However, at least a subset of the secondary bit arrays can supplement the primary array for all insertions. Default application of secondary arrays can reduce false positive errors, in particular false positive errors where the combined bit mask has K activated bits. In one variation, the method can include logging the key-value insertions and iterating over the key-value log to check for error scenarios. The key-value log can additionally be used in rebuilding a B-field data structure. Alternatively, a lookup verification can be completed after each insertion or verified during insertion.

Figure 9:
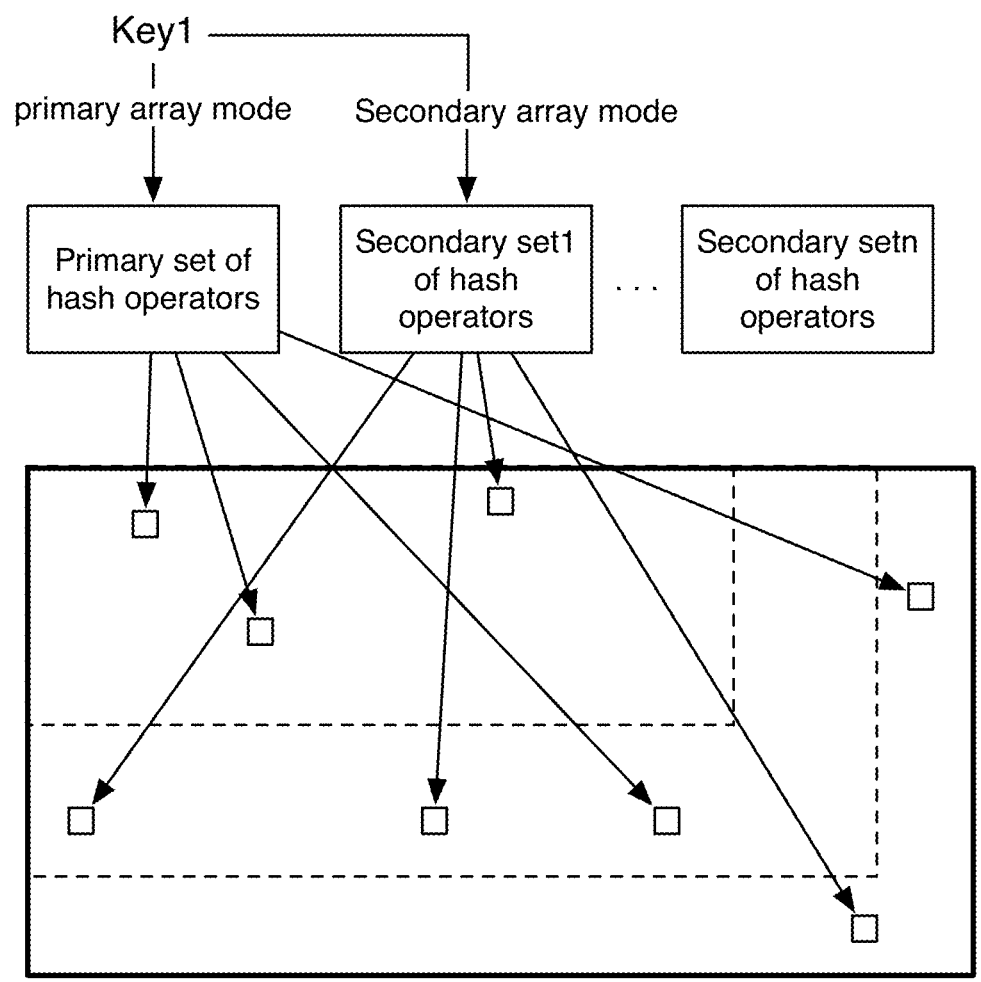
FIG. 9 is an schematic representation of a variation where the secondary array mode inserts/lookups elements in overlapping memory space.
Figure 10:
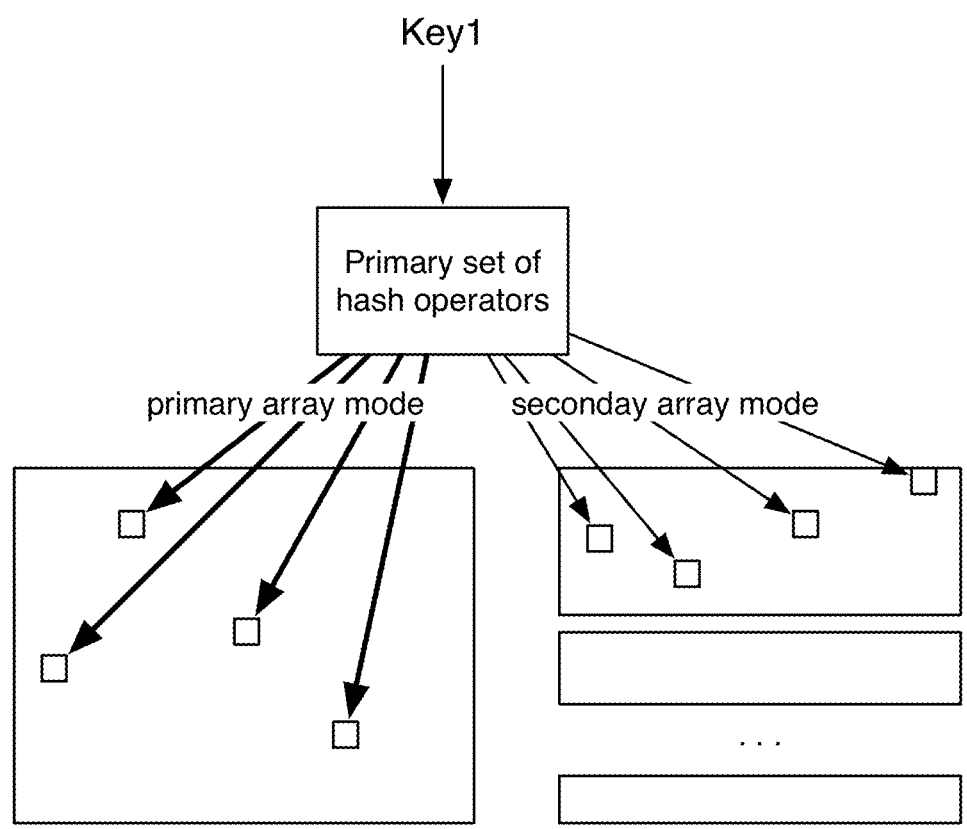
FIG. 10 is a schematic representation of a variation where the secondary array mode inserts/lookups elements in bit arrays in distinct memory arrays.

Block S520, which includes inserting the inserted key-value element in a secondary array mode, functions to add the element according to configuration of at least a second bit array. Secondary arrays can be configured according to various schema. In a first variation, a secondary bit array at least partially overlaps the primary bit array, and inserting the at least one key-value element into at least one secondary bit array includes using a secondary set of hash operators in place of the first hash operators, as shown in FIG. 9. The bit arrays may be sized larger to account for the overlapping bit arrays. Different hashing operators may generate different locations in memory to add the bit mask to the bit array. In another variation, initializing a bit array in memory can include initializing a set of secondary bit arrays in distinct memory locations of the computing platform, as shown in FIG. 10. The secondary bit arrays are allocated in a non-overlapping space in memory. Hash operators and bit masks can be kept the same space in memory. In some variations, the secondary bit arrays may be sized smaller to account for a smaller expected set size.

Block S530, which includes looking up a key in a secondary array mode, functions to look up a key in a secondary array. Looking up a key can be performed according to techniques similar to insertion. If an error scenario is detected in a first bit array, then a lookup operation is performed in a secondary array. Depending on the configuration of the secondary arrays, looking up a key in a secondary array mode can include looking up a key using a set of hash operators of a second array (or using alternative configuration properties) or looking up a key in a bit array in a distinct memory location.

Like the insertion techniques described above, when an error scenario occurs when looking up a key in a secondary array, a lookup operation is performed in a next secondary bit array. As described above, more than one secondary array may be used in a successive manner such that, in response to an indeterminate error scenario when inserting or looking up a key-value element in a secondary array, the inserting operation can include inserting or looking up the key-value element in a second secondary bit array (or in a third, fourth, etc. secondary bit array). However, any suitable number of secondary arrays can be implemented. The additional secondary arrays can be applied in a successive manner until a resolved value is found or the sequence of secondary arrays is exhausted.

3.5 Key Compression Process

Figure 12:
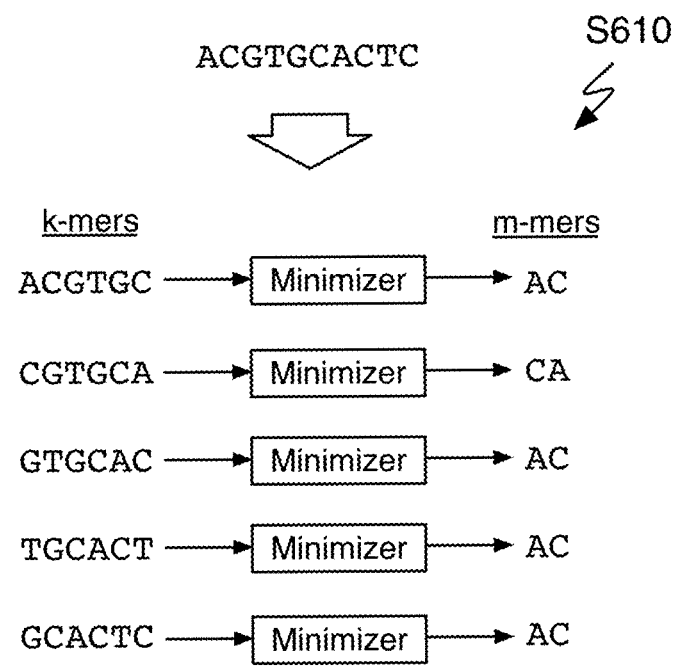
FIG. 12 is an exemplary schematic representation of a variation minimizing a key.
Figure 13A:
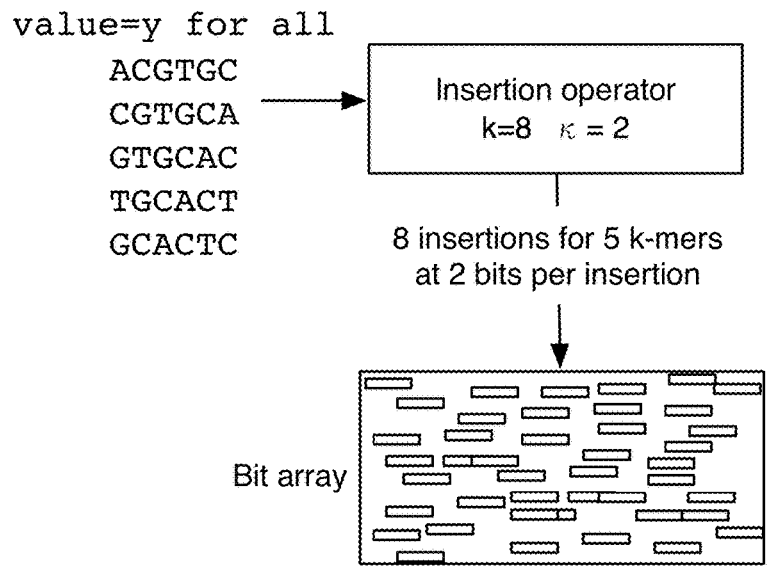
FIGS. 13A and 13B are exemplary schematic representations of space savings through key compression.
Figure 13B:
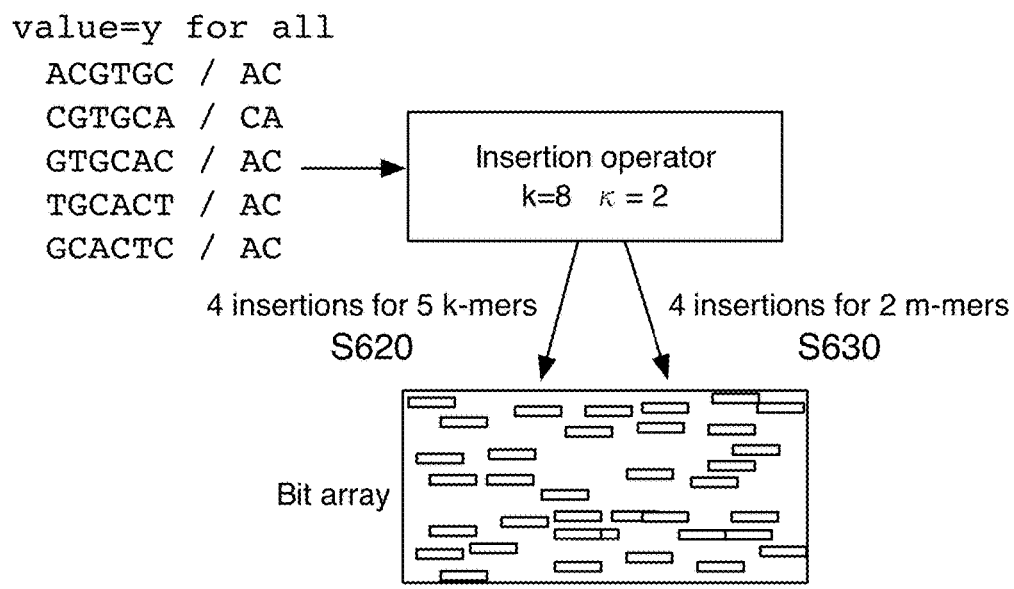

One variation of the insertion and lookup process can additionally include: minimizing a key in Block S610, as shown in FIG. 12; obtaining a first subset of indexes through a first subset of hash operators in Block S620; and obtaining a second subset of indexes through a second subset of hash operators in Block S630, as shown in FIG. 13B. The key compression process leverages compression properties of the keys to reduce the space required to store complete keys by storing lower information content of the keys alongside. The key compression process can be applied where a function can deterministically compress or reduce a set of keys with the same associated value into a smaller set, thereby reducing the number of unique pairings (e.g., [$x_1$=1, $x_2$=1, $x_3$=1, $x_4$=1]→[$y_1$=1, $y_2$=1, $y_1$=1, $y_1$=1]). The key compression can be implemented during the insertion process and the look up process.

In bioinformatics, a minimizer defines the lexicographically or otherwise smallest m-length sequence within a k-length k-mer. For example, a 10-length sequence "ACGTGCACTC" (SEQ ID NO: 1) can be enumerated over all of its k-mers and minimizers for k=6 and m=2. (In one example implementation, a five-megabase genome is enumerated over k-mers and minimizers, where k=31 and m=15.) The 2-length minimizer for the first k-mer "ACGTGC" is "AC", which is the lexicographically smallest of the sequences "AC", "CG", "GT", "TG", and "GC". The minimizer for the next k-mer "CGTGCA" is "CA", and the minimizer for the 3rd k-mer "GTGCAC" is again "AC". The key compression process functions to take advantage of the situation that: 1) there are fewer m-length minimizers possible than k-length k-mers; and 2) for longer, more practical k-mers (e.g., k greater than 20), the minimizers are unique and substantially non-random. For example, a given 14-length minimizer seen in six consecutive steps of a 31-length k-mer unique to a given Genome A can be unique to Genome A.

The compression process can apply a portion of the hash operators n to the full fragment (e.g., k-mer) and then to a second portion of hash operators on the minimizer. As the value space of the minimizers is smaller, there will exist greater redundancy in the key-value associations. Redundant insertions may not require additional space since the bits of the bit array have been activated in those locations.

Block S610, which includes minimizing a key, functions to calculate a deterministic compression of the key. In bioinformatics, minimizing a biological sequence k-mer calculates the lexicographically smallest m-length substring defined as a minimizer. The minimizer length can be configured, pre-defined, or set based on other method configurations.

Block, S620, which includes obtaining a first subset of indexes through a first subset of hash operators, functions to execute default insertion and/or lookup processes for a subset of the hashes. Block S630, which includes obtaining a second subset of indexes through a second subset of hash operators, functions to implement the minimizer with the other subset of hashes. The first and second subset of hash operators can be divided in half but may alternatively be divided according to any other suitable proportion. Because there are fewer unique minimizers than keys, there may exist redundant insertions across different distinct keys. As the key is used to obtain a set of indexes for insertion and lookup, Blocks S620 and S630 can be executed in both insertion and look up processes.

In the biological sequence use-case, the process of key compression can be expressed by: identifying a minimizing bioinformatics m-mer in a biological sequence k-mer of the set of key-value mappings; obtaining a first subset of indexes for the set of indexes by applying a first subset of hash operators to the biological sequence k-mer and obtaining a second subset of indexes for the set of indexes by applying a second subset of hash operators to the minimizing bioinformatics m-mer; identifying a minimizing bioinformatics m-mer in a biological sequence k-mer query; and obtaining a first subset of indexes for the set of query indexes by applying a first subset of hash operators to the biological sequence k-mer and obtaining a second subset of indexes for the second set of query indexes by applying a second subset of hash operators to the minimizing bioinformatics m-mer of the biological sequence query key.

In an exemplary scenario shown in FIGS. 13A and 13B, eight hash operators can be selected and the bit mask weight can be set to two such that k=8 and K=2. An insertion with this configuration can result in activation of 16 bits in the bit array. The five 6-mers of the 10-length sequence "ACGTGCACTC" (SEQ ID NO: 1) are all unique and thus can require up to 80 bits to be activated during a default operation, as illustrated in FIG. 13A. However, applying the key compression process, four of the 6-mers share a common minimizer ("AC"). The k-mers can be inserted with four hash operators and the minimizers can be inserted with another four hash operators. In the case in which the value association is the same for all k-mers, each unique k-mer can contain eight bits, and each unique minimizer can further contain eight bits. However, redundant insertions may not require marginal space because the bits were previously activated. Consequently, the upper bound on the space requirement for the foregoing case is reduced from 80 bits to 56 bits: 40 bits for the four full k-mer insertions and 16 bits for the two unique minimizers, as illustrated in FIG. 13B. Such space saving can vary empirically according to configured settings, though space saving of approximately 30% can be achieved in various practical scenarios.

3.6 Analysis Process

Figure 14:
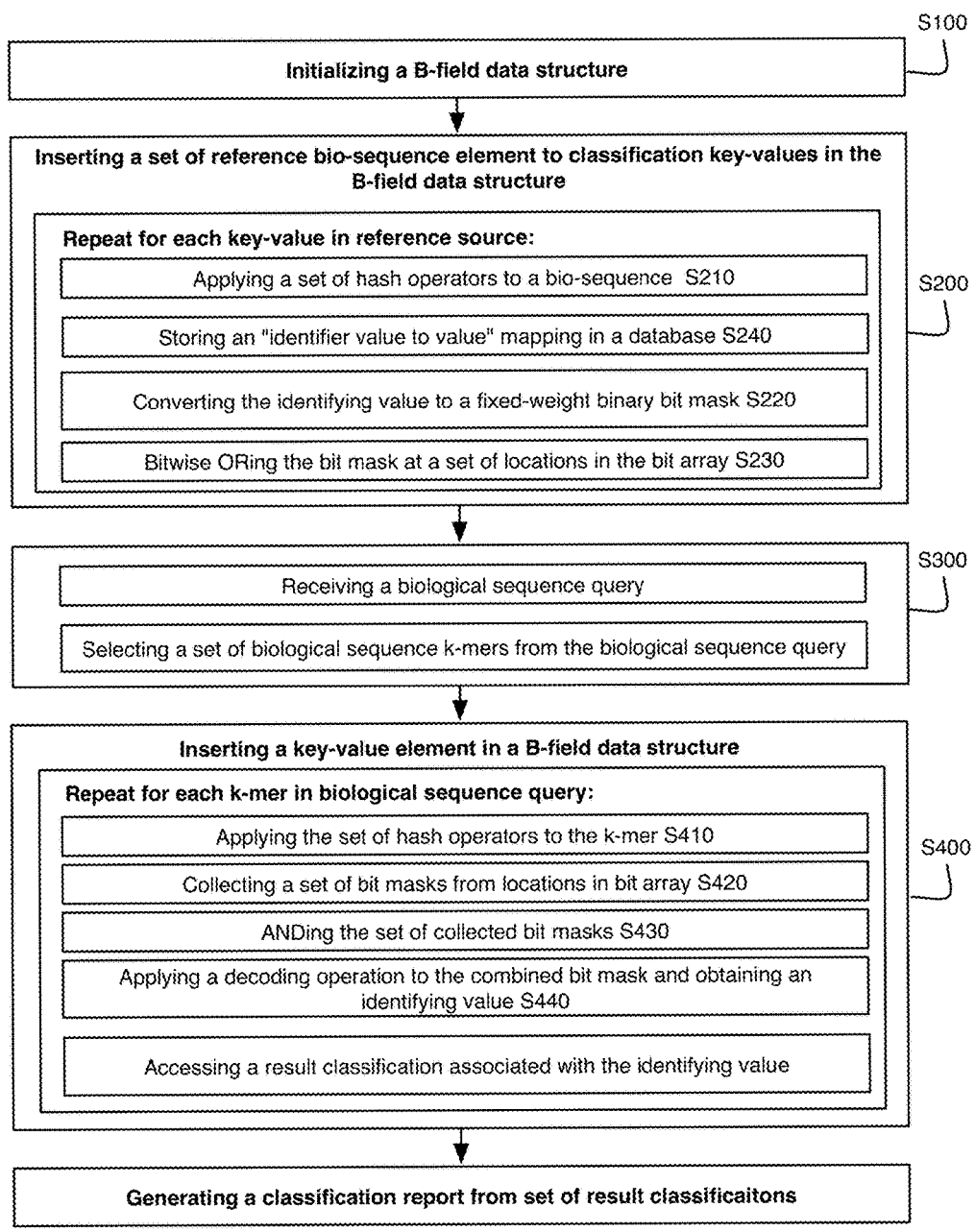
FIG. 14 is a detailed flowchart representation of variation applying the method to biological sequence dataset analysis.
Figure 16:
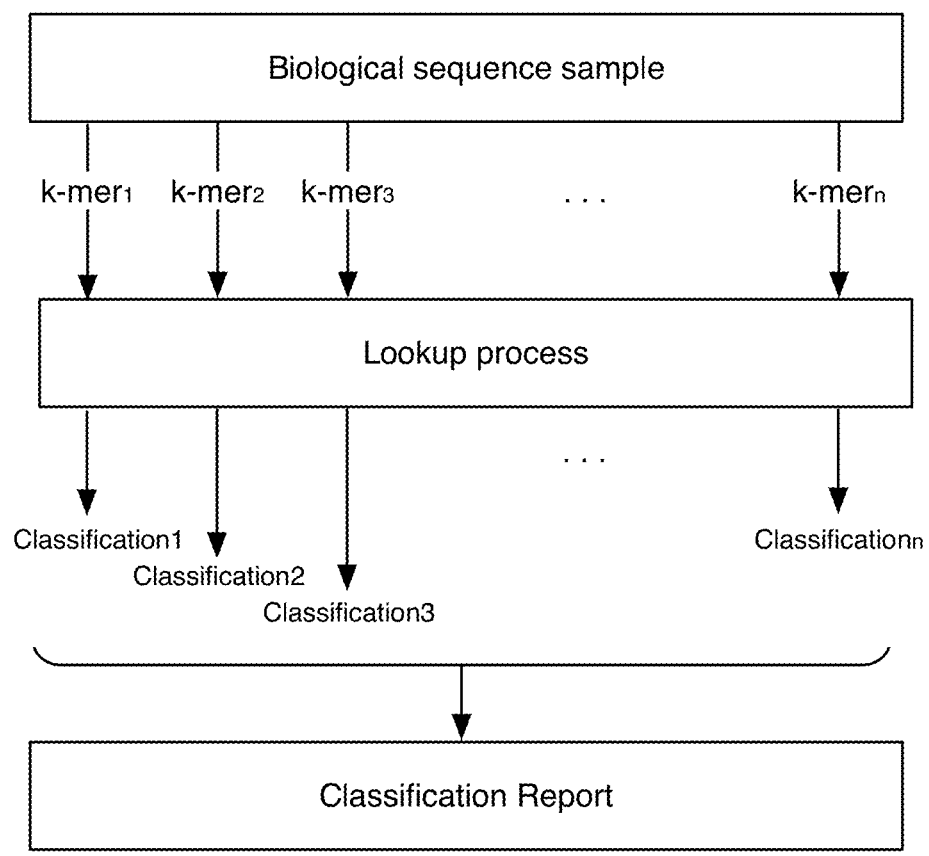
FIG. 16 is a schematic representation of a variation iterating through a set of lookups to generate a characterization report.

In one variation, the method is applied to biological sequence dataset analysis to execute a series of lookup operations while iterating over a set of k-mer substrings in the biological sequence dataset as shown in FIG. 14. In this variation, the method can include: receiving a biological sequence query and selecting a set of overlapping biological sequence k-mers from a dataset query as shown in FIG. 15; for the set of overlapping biological sequence k-mers, looking up a result characterization of each of the biological sequence k-mers through a bit array; and generating a characterization report based on a set of result characterizations, as shown in FIG. 16. Inserting and looking up an individual key-value element can be substantially similar to the process(es) described above, and any suitable variation of the method can be implemented in the analysis process.

In this foregoing variation, receiving a biological sequence query according to the method can include receiving a sequence dataset of length greater than the k-length k-mer. The sequence dataset can be the read output of a sequencing machine including A, C, T, G, and possibly other characters such as N and other IUPAC codes. In one example, a sequence data file is uploaded and processed to access the sequence data. The file may be in a common biological sequence format (e.g., FASTA, FASTQ files) and/or of any other suitable file format. In another variation, the sequence query can be entered in a text field.

Selecting a set of overlapping biological sequence k-mers from a dataset query according to the method functions to identify the sequence sub-strings that form the k-mers to be queried. In an example of a 10-length sequence "ACGTGCACTC" (SEQ ID NO: 1), the individual biological sequence 6-mers selected for the set of overlapping biological sequence k-mers include "ACGTGC", "CGTGCA", "GTGCAC", "TGCACT", and "GCACTC".

Once the set of overlapping biological sequence k-mers are selected, the method iterates over the set looking up a characterization (i.e., result value) for each k-mer. Specifically, for the set of overlapping biological sequence k-mers, the method looks up a result characterization of each of the biological sequence k-mers through a bit array. A set of result characterizations is thus generated during the look up process and a characterization report is thus generated. The characterization report can include a breakdown of characterizations found in the dataset. The characterization report can additionally or alternatively include indicators for the most prominent or for a set of most prominent characterizations found in the dataset. In yet another implementation, the characterization report can include a hierarchical summary of characterizations identified in the dataset.

4 B-Field Alternative Applications

The system and method have been thusly described from the perspective of applying the B-field data structure to biological sequencing use-cases. However, the system and method can alternatively be applied to other key-value storage use-cases. Generally, various use-cases of the system and method involve relatively large datasets, wherein the space complexity of O(1) and insertion/lookup operations of the foregoing data structure yields substantial benefits. Additionally, use-cases in which an applied dataset has existing errors, errors resulting from the probabilistic nature of the foregoing data structure can be relatively minimal. In one example use-case, scientific computing can implement the system and method for storing large quantities of data in relatively less space and with relatively faster access times. Furthermore, the error rates of the system and method can be relatively minimal compared with measurement error in the data.

In another use-case example, databases can implement the system and method to minimize disk accesses, network costs, and other computing costs. The databases can implement the system and method to store the location of database records locally (e.g., block info) or remotely (e.g., which shard of a database to query). The system and method can also be applied to multi-database or multi-table setups. The system and method can further be used to implement faster distributed joins and related database operations. In one example, storing over a billion arbitrary length URL keys and a number value in the domain of $\{1 \ldots 1000\}$ requires approximately 7.1 gigabytes (GB) at an error rate of alpha=$2^{-32}$ ($p \approx 2^{-14.1}$) and $\beta=0$.

The system and method can also support various local data use-cases. In particular, more data can be stored for a given memory allocation, and these data can be stored closer to a client at a lower space or network cost. In one example, a rich list of malicious websites can be stored within every browser, thereby supporting a more nuanced security environment that details classes of risks and associated precautions rather than simply a binary on/off warning system.

A core feature of the B-field system and method includes supporting probabilistic key-value storage in a relatively space- and time-efficient manner. Per the use-case, this data structure can be extended as needed. Several sample extensions can include cache locality optimizations, scalability optimizations, space efficiency optimizations, and alternative encoding schemes.

Cache locality optimizations can include using the first hash to select a cache-sized block from m$\kappa$-bit array and then hashing to locations within that block or subsection of the bit array.

Scalability optimizations can include splitting an m$\kappa$-bit array across multiple machines, such as in blocks or in a strided fashion.

Space efficiency optimizations can include: if a large percentage of S maps to y values with a smaller maximum value $\theta$, store that percent of S in a B-field built with lower v and $\kappa$ values while storing the remaining elements in a second B-field. Such techniques can extend to arbitrary depth and enable use combinations of B-fields to further encode y values.

Alternative encoding scheme optimizations can implement a different encoding scheme, such as those with built-in error correction. Error-correction can thus be implemented at both the decoding step and via the use of a set of B-field arrays (e.g., $Array_0$ and $Array_1$).

The system, method, and variations thereof can be embodied and/or implemented at least in part as a machine configured to receive a computer-readable medium storing computer-readable instructions. The instructions can be executed by computer-executable components integrated with the B-field data structure processing system. The computer-readable medium can be stored on any suitable computer-readable media such as RAMs, ROMs, flash memory, EEPROMs, optical devices (CD or DVD), hard drives, floppy drives, or any suitable device. The computer-executable component can be a general or application specific processor, but any suitable dedicated hardware or hardware/firmware combination device can alternatively or additionally execute the instructions.

As a person skilled in the art will recognize from the previous detailed description and from the figures and claims, modifications and changes can be made to the embodiments of the invention without departing from the scope of this invention defined in the following claims.

I claim:

1. A method for storing classified biological sequence key-value elements in a data structure and generating a characterization report of a biological sequence query, the method comprising using a processor of a computing platform and the processor thereby:

assigning a size of a primary bit array of a probabilistic data structure, the size being assigned in association with a desired maximum false positive rate and an expected number of key-value elements to be stored in a probabilistic data structure;

assigning a count of hash operators of the probabilistic data structure;

assigning at least one encoding operator of the probabilistic data structure, the encoding operator having a bit mask output with an assigned mask size and a mask weight, wherein the weight is the number of activated bits;

allocating memory of the computing platform such that the allocated memory is sufficient to store the primary bit array according to the assigned size of the primary bit array;

iteratively storing instances of the key-value elements in the primary bit array, wherein each instance of the key-value elements comprises a biological sequence k-mer key and a biological classification value paired to the key, and wherein each iteration of the storing further comprises the following steps with respect to the storing of each instance of the key-value elements:

applying the hash operators to the biological sequence k-mer of an instance thereby obtaining a set of indexes particular to the key, determining insertion locations in the primary bit array according to the set of indexes, executing the at least one encoding operator on the value of the instance, thereby converting the value to a particular bit mask having the assigned mask size and the assigned mask weight, and activating a set of bits in the primary bit array with the bit mask at the insertion locations;

obtaining the biological sequence query comprising a set of overlapping biological sequence k-mers;

iteratively extracting instances of k-mer characterizations for each biological sequence k-mer in the set of overlapping biological sequence k-mers, and wherein each iteration of the extracting further comprises the following steps with respect to the extracting of each instance of the set of overlapping biological sequence k-mers:

applying the hash operators to the biological sequence k-mer of an instance thereby obtaining query indexes, determining query locations in the primary bit array according to the query indexes, retrieving stored bit masks from the query locations, bitwise ANDing the stored bit masks into a combined bit mask, and decoding the combined bit mask into a k-mer characterization of the instance; and generating the characterization report of the biological sequence query from the instances of k-mer characterizations.

2. The method of claim 1, wherein storing at least one instance of a key-value element when iteratively storing instances of the key-value elements in the primary bit array, further comprises:

detecting an indeterminate error scenario for a key-value mapping; and, in response to the indeterminate error scenario, storing the at least one instance of a key-value element in a secondary bit array; and wherein extracting an instance of a k-mer characterization further comprises: in response to detection of an indeterminate error scenario for a biological sequence k-mer in the primary bit array, extracting a k-mer characterization of the biological sequence k-mer in the secondary bit array.

3. The method of claim 2, wherein the allocated memory is further sufficient to store the primary bit array and the secondary bit array in distinct memory locations of a computing platform.

4. The method of claim 2, wherein storing the first key-value element into the secondary bit array further comprises: applying a secondary set of hash operators to the reference biological sequence k-mer and thereby obtaining a second set of indexes; determining secondary insertion locations in the secondary bit array according to the second set of indexes; and bitwise ORing the bit mask at secondary insertion locations of the secondary bit array; and wherein the secondary bit array overlaps the primary bit array in memory.

5. The method of claim 1, further comprising:

identifying a minimizing bioinformatics m-mer for biological sequence k-mers in the key-value elements;

wherein applying the hash operators to the biological sequence k-mer of an instance when storing further comprises applying a first subset of hash operators to the biological sequence k-mer of the instance and thereby obtaining a first subset of indexes for the set of indexes and applying a second subset of hash operators to the minimizing bioinformatics m-mer and thereby obtaining a second subset of indexes for the set of indexes;

identifying a minimizing bioinformatics m-mer in a biological sequence k-mer of the set of overlapping biological sequence k-mers; and wherein applying the hash operators to the biological sequence k-mer of an instance when extracting instances of k-mer characterizations further comprises applying the first subset of hash operators to the biological sequence k-mer of the instance thereby obtaining a first subset of the query indexes and applying the second subset of hash operators to the minimizing bioinformatics m-mer of the biological sequence k-mer thereby obtaining a second subset of the query indexes.

6. The method of claim 1, wherein allocating memory of the computing platform comprises allocating memory in an internet-accessible distributed computing environment.

7. The method of claim 1, wherein the biological sequence k-mers are nucleotide sequence k-mers.

8. The method of claim 1, wherein the biological sequence k-mers are protein sequence k-mers.

9. The method of claim 1, wherein generating the characterization report comprises generating a summary of biological classifications identified in the instances of k-mer characterizations.

10. The method of claim 1, wherein the allocated memory is at least a gigabyte of memory.

11. A method for storing reference key-value elements in a data structure and then retrieving a result value using a query key, the method comprising using a processor of a computing platform and the processor thereby:

assigning a size of a primary bit array of a probabilistic data structure, the size being assigned in association with a desired maximum false positive rate and an expected number of reference key-value elements to be stored in a probabilistic data structure;

assigning a maximum value of the possible values within the reference key-value elements to be stored in the probabilistic data structure;

assigning a count of hash operators of the probabilistic data structure;

assigning at least one encoding operator of the probabilistic data structure, the encoding operator having a bit mask output with an assigned mask size and a mask weight, wherein the weight is the number of activated bits;

allocating memory of the computing platform such that the allocated memory is sufficient to store the primary bit array according to the assigned size of the primary bit array;

iteratively storing instances of the reference key-value elements in the primary bit array, wherein each instance of the reference key-value elements comprises a key that is a biological sequence fragment and a value paired to the key, and the value being a biological characterization value within the maximum value range, and wherein each iteration of the storing further comprises the following steps with respect to the storing of each instance of the reference key-value elements:

applying the hash operators to the key of an instance thereby obtaining a set of indexes particular to the key, determining insertion locations in the primary bit array according to the set of indexes, executing the encoding operator on the value of the instance, thereby converting the value to a particular bit mask having the assigned mask size and the assigned mask weight, and activating a set of bits in the primary bit array through bitwise ORing the bit mask at the insertion locations;

obtaining a query key, the query key being a biological sequence fragment; and extracting a result value for the query key from the primary bit array, by:

applying the hash operators to the query key and thereby obtaining query indexes;

determining query locations in the primary bit array according to the query indexes;

retrieving stored bit masks from the query locations;

bitwise ANDing the stored bit masks into a combined bit mask; and applying a decoding operation to the combined bit mask and thereby obtaining the result value.

12. The method of claim 11, further comprising: detecting an indeterminate error scenario of the primary bit array in response to storing an instance of a reference key-value element in the primary bit array; and, in response to detecting an indeterminate error scenario, storing the reference key-value element into a secondary bit array.

13. The method of claim 12, wherein the allocated memory is further sufficient to store the primary bit array and the secondary bit array in distinct memory locations of the computing platform.

14. The method of claim 12, wherein storing the reference key-value element into the secondary bit array further comprises: applying secondary hash operators to the reference key thereby obtaining a second set of indexes; determining secondary insertion locations according to the second set of indexes; and activating a set of bits in the primary bit array through bitwise ORing the bit mask at secondary insertion locations of the secondary bit array; and wherein the secondary bit array overlaps the primary bit array in memory.

15. The method of claim 12, further comprising: detecting a second indeterminate error scenario of the secondary bit array in response to storing the reference key-value element into the secondary bit array; and, in response to detecting the second indeterminate error scenario, storing the reference key-value element into a second secondary bit array.

16. The method of claim 11, further comprising identifying a minimized key for a set of keys in reference key-value elements; and wherein obtaining the set of indexes further comprises obtaining a first subset of indexes for the set of indexes by applying a first subset of hash operators to the key and obtaining a second subset of indexes for the set of indexes by applying a second subset of hash operators to the minimized key.

17. The method of claim 16, wherein obtaining the query indexes further comprises obtaining a first subset of the query indexes by applying a first subset of hash operators to the key and obtaining a second subset of the query indexes by applying a second subset of hash operators to the minimized key of the query key.

18. The method of claim 11, wherein storing instances of the reference key-value elements in the primary bit array further comprises storing a first set of reference key-value elements in the primary bit array at a first time instance; and further comprising storing a second set of reference key-value elements in the primary bit array at a second time instance succeeding the first time instance.

19. The method of claim 11, wherein allocating memory of the computing platform comprises allocating memory within an internet-accessible distributed computing environment.

20. The method of claim 19, wherein allocating memory within the internet-accessible distributed computing environment comprises sharding the primary bit array across a set of computing resources in the distributed computing environment.

21. The method of claim 11, wherein the allocated memory is at least a gigabyte of memory.

22. A method for storing classified biological sequence k-mer data as key-value elements in a data structure and then retrieving a classification result using a k-mer query, the method comprising using a processor of a computing platform and the processor thereby:

assigning a size of a primary bit array of a probabilistic data structure, the size being assigned in association with a desired maximum false positive rate and an expected number of key-value elements to be stored in a probabilistic data structure;

assigning a maximum value of the possible values within the key-value elements to be stored in the probabilistic data structure;

assigning a count of hash operators of the probabilistic data structure;

assigning at least one encoding operator of the probabilistic data structure, the encoding operator having a bit mask output with an assigned mask size and a mask weight, wherein the weight is the number of activated bits;

allocating memory of the computing platform such that the allocated memory is sufficient to store the primary bit array according to the assigned size of the primary bit array, wherein the allocated memory is at least a gigabyte of memory;

iteratively storing instances of the key-value elements in the primary bit array, wherein each instance of the key-value elements comprises a biological sequence k-mer key and a biological classification value paired to the key, and the biological classification value being an identifier within the maximum value range, and wherein each iteration of the storing further comprises the following steps with respect to the storing of each instance of the key-value elements:

applying the hash operators to the biological sequence k-mer of an instance thereby obtaining a set of indexes particular to the key, determining insertion locations in the primary bit array according to the set of indexes, executing the encoding operator on the value of the instance, thereby converting the value to a particular bit mask having the assigned mask size and the assigned mask weight, and activating a set of bits in the primary bit array through bitwise ORing the bit mask at the insertion locations;

obtaining a query key that is a biological sequence k-mer; and extracting a biological characterization result value for the query key from the primary bit array, by:

applying the hash operators to the query key and thereby obtaining a set of query indexes, determining query locations in the primary bit array according to the set of query indexes, retrieving stored bit masks from the query locations, bitwise ANDing the stored bit masks into a combined bit mask, and applying a decoding operation to the combined bit mask and thereby obtaining the result value.

23. The method of claim 22, further comprising: detecting an indeterminate error scenario of the primary bit array in response to inserting a key-value element into the primary bit array; and, in response to detecting an indeterminate error scenario, storing the key-value element into a secondary bit array.

24. The method of claim 22, allocating memory of the computing platform comprises allocating memory within an internet-accessible distributed computing environment.

25. The method of claim 24, allocating memory within the internet-accessible distributed computing environment comprises sharding the primary bit array across a set of computing resources in the distributed computing environment.

* * * * *